(12) United States Patent
Huq et al.

(10) Patent No.: US 9,151,205 B2
(45) Date of Patent: Oct. 6, 2015

(54) REAL-TIME SOOT MEASUREMENT IN A DIESEL PARTICULATE FILTER

(71) Applicant: Indiana University Research & Technology Corporation, Indianapolis, IN (US)

(72) Inventors: Ragibul Huq, Indianapolis, IN (US); Sohel Anwar, Carmel, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 0 days.

(21) Appl. No.: 14/182,039

(22) Filed: Feb. 17, 2014

(65) Prior Publication Data
US 2014/0230532 A1    Aug. 21, 2014

Related U.S. Application Data

(60) Provisional application No. 61/765,469, filed on Feb. 15, 2013.

(51) Int. Cl.
*F01N 11/00* (2006.01)
*G01N 15/08* (2006.01)

(52) U.S. Cl.
CPC ............. *F01N 11/00* (2013.01); *G01N 15/08* (2013.01); *F01N 2560/00* (2013.01); *F01N 2900/1606* (2013.01); *G01N 2015/084* (2013.01); *G01N 2015/0853* (2013.01); *Y02T 10/47* (2013.01)

(58) Field of Classification Search
CPC ............. F01N 11/00; F01N 2560/00; F01N 2900/1606; G01N 15/08; G01N 2015/084; G01N 2015/0853; Y02T 10/47
USPC ........................................................ 73/114.69
See application file for complete search history.

(56) References Cited

U.S. PATENT DOCUMENTS

| | | | | |
|---|---|---|---|---|
| 4,656,832 | A | * | 4/1987 | Yukihisa et al. ............... 60/303 |
| 5,157,340 | A | | 10/1992 | Walton et al. |
| 5,423,904 | A | * | 6/1995 | Dasgupta ........................ 96/146 |
| 7,434,449 | B2 | | 10/2008 | Kursaka et al. |
| 7,707,875 | B2 | | 5/2010 | Lee |
| 7,870,779 | B2 | | 1/2011 | Lattin et al. |
| 8,015,862 | B2 | | 9/2011 | Bollinger et al. |

(Continued)

FOREIGN PATENT DOCUMENTS

| | | | | |
|---|---|---|---|---|
| JP | 2003269134 | | 9/2003 | |
| JP | 2003301711 | | 10/2003 | |
| WO | WO 9308382 A1 | * | 4/1993 | ............... F01N 3/02 |

*Primary Examiner* — Freddie Kirkland, III
(74) *Attorney, Agent, or Firm* — John V. Daniluck; Bingham Greenebaum Doll LLP

(57) ABSTRACT

Methods and apparatus for detecting the filtering state of a filter, such as a particulate filter. Some embodiments include one or more capacitive sensors that provide a signal corresponding to the filtered state of the filter with a change in measured capacitance. A novel ECT based sensing technique for soot load estimation in a diesel particulate filter is presented. The sensing technology is based on principle that deposited soot thickness inside DPF causes a variation in the dielectric constant which has a direct impact on the capacitance of ECT system and its output voltage. The sensor can be built into the DPF outer shell as indicated in the design. The simulation results demonstrate that there is a direct relationship between the amount of soot load in the DPF and the output voltage of the ECT system which can be used to estimate the soot load.

21 Claims, 30 Drawing Sheets

(56) References Cited

U.S. PATENT DOCUMENTS

| | | | |
|---|---|---|---|
| 8,210,033 B2 * | 7/2012 | Kondo et al. | 73/114.69 |
| 8,225,684 B2 * | 7/2012 | Kondo et al. | 73/865.8 |
| 8,549,846 B2 * | 10/2013 | Gonze et al. | 60/297 |
| 8,679,413 B2 * | 3/2014 | Ishihara | 422/174 |
| 8,783,112 B2 * | 7/2014 | Korenev | 73/753 |
| 2006/0144124 A1 | 7/2006 | Kusaka et al. | |
| 2008/0264146 A1 | 10/2008 | Roesch et al. | |
| 2009/0126458 A1 | 5/2009 | Fleischer et al. | |
| 2010/0308849 A1 * | 12/2010 | Bouteiller et al. | 324/700 |
| 2012/0076699 A1 * | 3/2012 | Ishihara | 422/174 |
| 2012/0234172 A1 | 9/2012 | Sugiyama et al. | |

\* cited by examiner

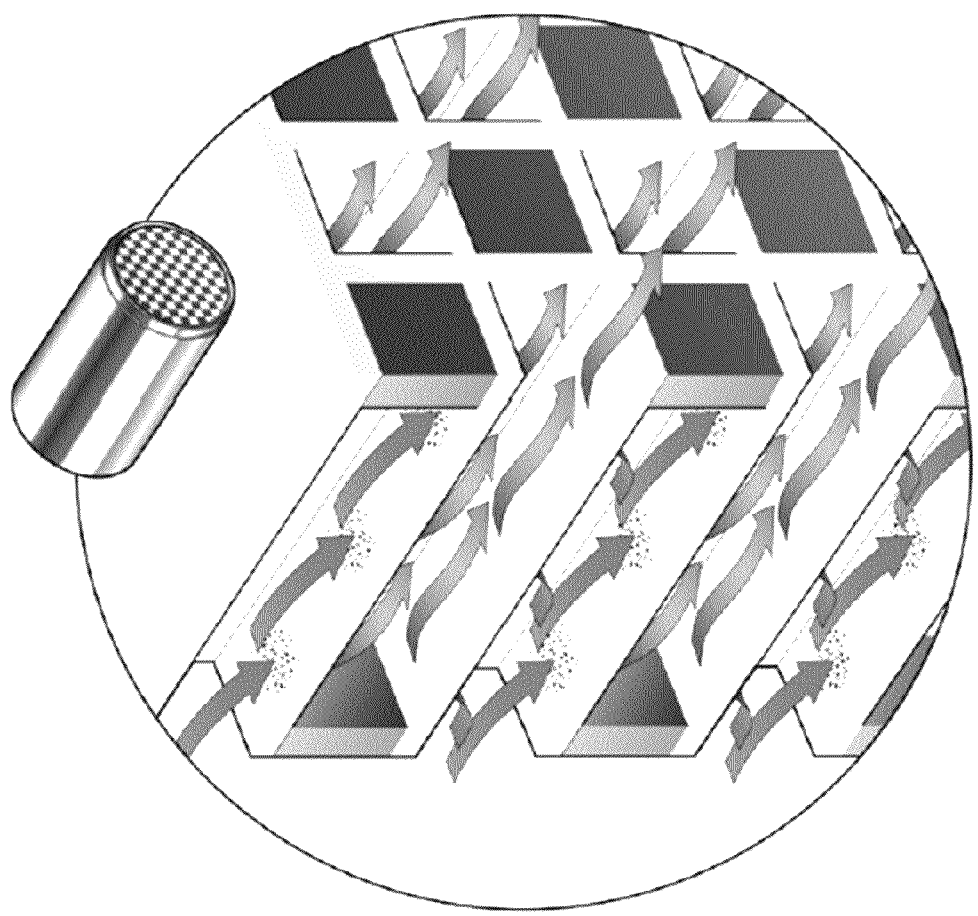

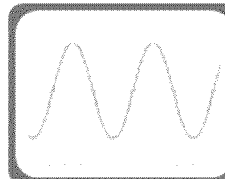 Sine wave generator
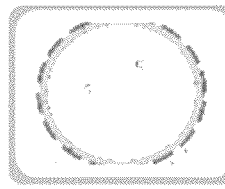 ECT electrode sensor
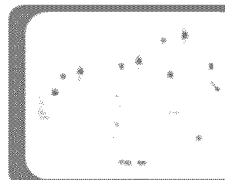 Signal conditioning system
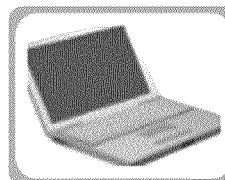 Central control unit
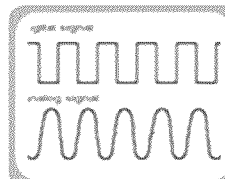 Digital signal
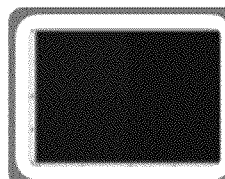 Image reconstruction
FIG. 2-5

REAL-TIME SOOT MEASUREMENT IN A DIESEL PARTICULATE FILTER

CROSS REFERENCE TO RELATED APPLICATION

This application claims the benefit of priority to U.S. Provisional Patent Application Ser. No. 61/765,469, filed Feb. 15, 2013, incorporated herein by reference.

FIELD OF THE INVENTION

Various embodiments of the present invention pertain to the monitoring and control of filters, and some embodiments to the monitoring and control of particulate filters, especially for diesel engines.

BACKGROUND OF THE INVENTION

Diesel engines are widely used in heavy duty trucks and off road vehicles due to their fuel efficiency and high power outputs. Environmental regulatory agencies have pushed ever stringent regulations on all internal combustion engines, including Diesel engines on gaseous as well as particulates (soot) emissions. In order to meet today's and tomorrow's stringent emission requirements, modern diesel engines are equipped with diesel particulate filters (DPF's), as well as onboard technologies to evaluate the status of DPF. In course of time, particulate matter (soot) will be deposited inside the DPFs which tend to clog the filter and hence generate a back pressure in the exhaust system, negatively impacting the fuel efficiency. To remove the soot build-up, regeneration (active or passive) of the DPF must be done as an engine exhaust after treatment process at pre-determined time intervals. Since the regeneration process consume fuel, a robust and efficient operation based on accurate knowledge of the particulate matter deposit (or soot load) becomes essential in order to keep the fuel consumption at a minimum.

Diesel engines have come a long way in the area of emission control technologies in the last couple of decades. One of the areas in which engine technology made great strides is in the reduction of particulate matter (PM) emissions via diesel particulate filter (DPF). However, as the PM or soot is retained by the filter, the filter passageway increasingly becomes more restrictive resulting in elevated back pressure in the exhaust. This furthers results in lower fuel efficiency for the engines since the pistons have to exert more pressure to purge the exhaust gas.

One effective way to address this problem is to burn the soot load in the DPF periodically either by injecting more fuel in the engine or by a separate combustor upstream of the DPF with the aid of a diesel oxidation catalyst (DOC). The latter is known as active regeneration of DPF and is commonly used for DPF. Here a fuel doser is used to raise the exhaust gas temperature to burn off the soot load in DPF. The timing and amount of fuel dosing is critical in ensuring optimal performance of DPF functions.

The performance efficiency of a DPF with active regeneration is dependent on the accuracy of soot load estimation. Current soot load estimation is based on differential pressure measurement across the DPF whose accuracy can vary up to 50% from the true soot load. As a result, fuel dosing for active regeneration may not be optimal. This can result in significant loss in fuel efficiency if the estimate is higher than real value (since more fuel need be used), or in serious DPF damage if the estimate is less than the real value when the filter may be nearly clogged. In the latter scenario, there is also a fuel penalty due to increased back pressure in the exhaust. Also, fuel dosing for active regeneration may not be optimal. It has been shown that fuel penalty caused by regeneration (2.2% to 5.3%) can be more than fuel penalty due to backpressure (1.8% to 2.2%).

Diesel particulate filters were first used in the 1980's to remove the particulate matter/soot from the exhaust of the Diesel engine with an efficiency level of 90% or more. These filters are mostly made of ceramic materials and can withstand high temperatures. The deposited soot in the filter cavities may result in higher back pressure causing overall efficiency of the diesel engine to drop by as much as 2%. Also, a clogged filter may fail prematurely. As a result, the deposited soot in the DPF is periodically cleaned, generally by means of a process of regeneration or burning out the soot. In active regeneration, fuel is injected in a chamber right before the DPF, thus raising the exhaust temperature high enough to burn the soot inside DPF cavities. Other methods, such as microwave heating, have been proposed to clean the DPF. Fuel dosing remains the most prevalent method of active regeneration. The timing and amount of fuel dosing is critical in ensuring optimal performance of DPF functions. As a result, fuel dosing for active regeneration may not be optimal.

What is needed are improved methods for detecting the flow capability of a diesel particulate filter. An instantaneous soot load sensor based on electrical capacitance sensor is shown and described herein, and also regeneration systems utilizing such a sensor, in various embodiments of the present invention as an alternative for soot load estimation.

SUMMARY OF THE INVENTION

Various embodiments of the present invention pertain to a sensing method for a DPF that can accurately measure in-situ soot load using Electrical Capacitance Tomography (ECT). Simulation results show that such methods offer an effective way to accurately estimate the soot load in DPF. Such methods are expected to have a profound impact in improving overall PM filtering efficiency (and thereby fuel efficiency), and durability of a Diesel Particulate Filter (DPF) through appropriate closed loop regeneration operation.

Various embodiments of the present invention pertain to the use of electrical capacitance tomography to measure the soot load in DPF. Further, various embodiments disclose the use of a closed loop active regeneration system with feedback from such sensors. In order to improve overall fuel efficiency, it is useful to integrate the electrical capacitance sensor in a closed loop control system for active regeneration for optimal fuel dosing and back pressure regulation. Such closed loop active regeneration system is also expected to have significant impact on filter diagnostics sensor data integration into OBD II (On-Board Diagnostics II). Another benefit of such closed loop system is damage/failure prevention of the DPF by appropriate soot load monitoring and control, including detection and accommodation of the aging of the DPF (or other environmental conditions) while maintaining high performance efficiency of PM filtering. In addition to environmental benefits in meeting regulatory PM emission limits, a closed loop actively regenerated DPF system with parameter adaptation can provide good performance for a wider range of environmental conditions. On the economic front, this project will help the OEMs in developing new commercial DPF products with such cutting-edge technology and thus generating new US jobs while maintaining World leadership in the enabling engine technology area.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

FIG. 13A-FIG. 13F show various tomographic images of the test results noted in FIG. 11 using linear back-projection.

FIG. 2-1 shows porous walls of a DPF.

FIG. 2-2 is a graphical representation of DPF diagnosis regulatory requirements.

FIG. 2-3 is a graphical representation of a permittivity model of components in series, being empty, completely filled, and partially filed.

FIG. 2-4 is a graphical representation of a parallel permittivity model, showing empty, completely filled, and partially filled components.

FIG. 2-5 is a flow chart showing electrical capacitance tomography systems.

FIG. 2-7 is a square pixel grid.

FIG. 2-9 is a graphical representation of real part dielectric constant and soot layer thickness.

FIG. 2-10 shows the relationship between output voltage and capacitance.

FIG. 2-11 shows a 5V AC input in 60 pF capacitor circuit.

FIG. 2-12 shows an output voltage 0.6-1.7 v for 5 μs.

FIG. 2-13 shows a 5V AC input in 90 pF capacitor circuit.

FIG. 2-14 shows an output voltage 0.9-1 vb for 5 μs.

FIG. 2-15 shows a 5V AC input in 130 pF capacitor circuit.

FIG. 2-16 shows an output voltage 0.5=–0.6 v for 5 μs.

FIG. 2-17 shows (a) 4 capacitor plate positions in ECT and (b) 2*2 pixel grid.

FIG. 2-18 shows a sensitivity matrix.

FIG. 2-19 shows a particulate deposition.

FIG. 2-20 shows a tomographic image.

ELEMENT NOMENCLATURE

Figure 1A:
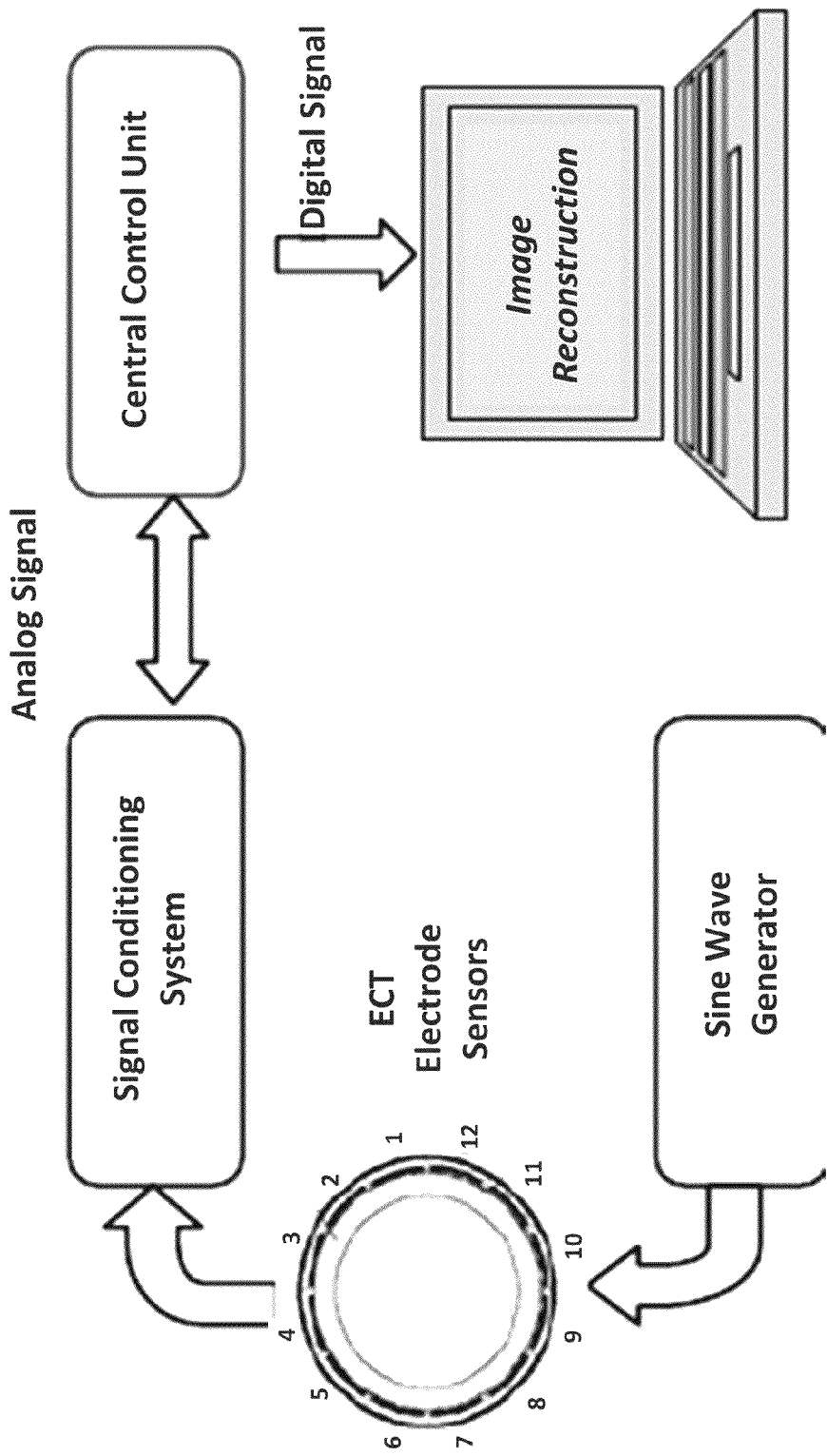
FIG. 1A shows an electrical capacitance tomography system.

| | |
|---|---|
| 1 | exiting electrode |
| 2 | exiting electrode |
| 10 | engine |
| 11 | fuel system |
| 12 | source |
| 13 | component (also injector; fuel doser) |
| 14 | heating member (also catalyst, chamber) |
| 16 | filter |
| 20 | system |
| 21 | housing |
| 30 | sensor |
| 32 | plate |
| 34 | plates (electrodes) |
| 60 | controller |
| 62 | driver |
| 66 | processor |
| 80 | algorithm |
| 82 | soot estimator |
| 84 | predictor |

VARIABLE NOMENCLATURE

| | |
|---|---|
| v | Potential difference |
| d | Distance between two plates |
| E | Electric field strength between the plates |
| $\epsilon$ | Permittivity |
| In vacuum, the value of $\epsilon$:$\epsilon_o$ = 8.854*10$^{-12}$ F/m | |
| $\epsilon_r$ | Relative permittivity |
| C | Charge |
| Effective permittivity in: | |
| Series Permittivity Model: $\epsilon_s$ | |
| Parallel Permittivity Model: $\epsilon_p$ | |
| Maxwell Garnett Permittivity Model: $\epsilon_m$ | |
| [S] | Sensitivity matrices |
| [K] | Normalized pixel permittivity's matrix |
| [C] | Normalized electrode-pair capacitances |
| $\epsilon_b$ | Relative permittivity of a base dielectric |
| $\epsilon_i$ | Relative permittivity of the i-th sort of inclusions |
| $f_i$ | Volume fraction occupied by the inclusion of the i-th sort |
| $N_{ik}$ | Depolarization factors of the i-th sort of inclusions |
| Index k = 1, 2, 3 corresponds to x, y, and z Cartesian coordinates | |
| $T_O$: $\rho_o$ | Resistivity at temperature |

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments.

The use of an N-series prefix for an element number (NXX.XX) refers to an element that is the same as the non-prefixed element (XX.XX), except as shown and described thereafter. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. This description convention also applies to the use of prime ('), double prime ("), and triple prime ('") suffixed element numbers. Therefore, it is not necessary to describe the features of 20.1, 20.1', 20.1", and 20.1'" that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

What will be shown and described herein, along with various embodiments of the present invention, is discussion of one or more tests that were performed. It is understood that such examples are by way of examples only, and are not to be construed as being limitations on any embodiment of the present invention. It is understood that embodiments of the present invention are not necessarily limited to or described by the mathematical analysis presented herein.

Various references may be made to one or more processes, algorithms, operational methods, or logic, accompanied by a diagram showing such organized in a particular sequence. It is understood that the order of such a sequence is by example only, and is not intended to be limiting on any embodiment of the invention.

Diesel particulate filters were first used in the 1980's which remove the particulate matter/soot from the exhaust of the Diesel engine with an efficiency level of 90% or more. The most commonly used DPFs are porous ceramic wall-flow filters, as shown schematically in FIG. 2-1. Refractory materials such as silicon carbide, cordierite or aluminum-titanate are used for this purpose. Silicon carbide filters dominate the market owing to the material's mechanical strength and high thermal stability. Alternate channels are plugged, forcing the exhaust through the porous channel walls. The gaseous exhaust passes through the porous walls, but particulate matter (PM) is trapped in the filter.

Figure 2:
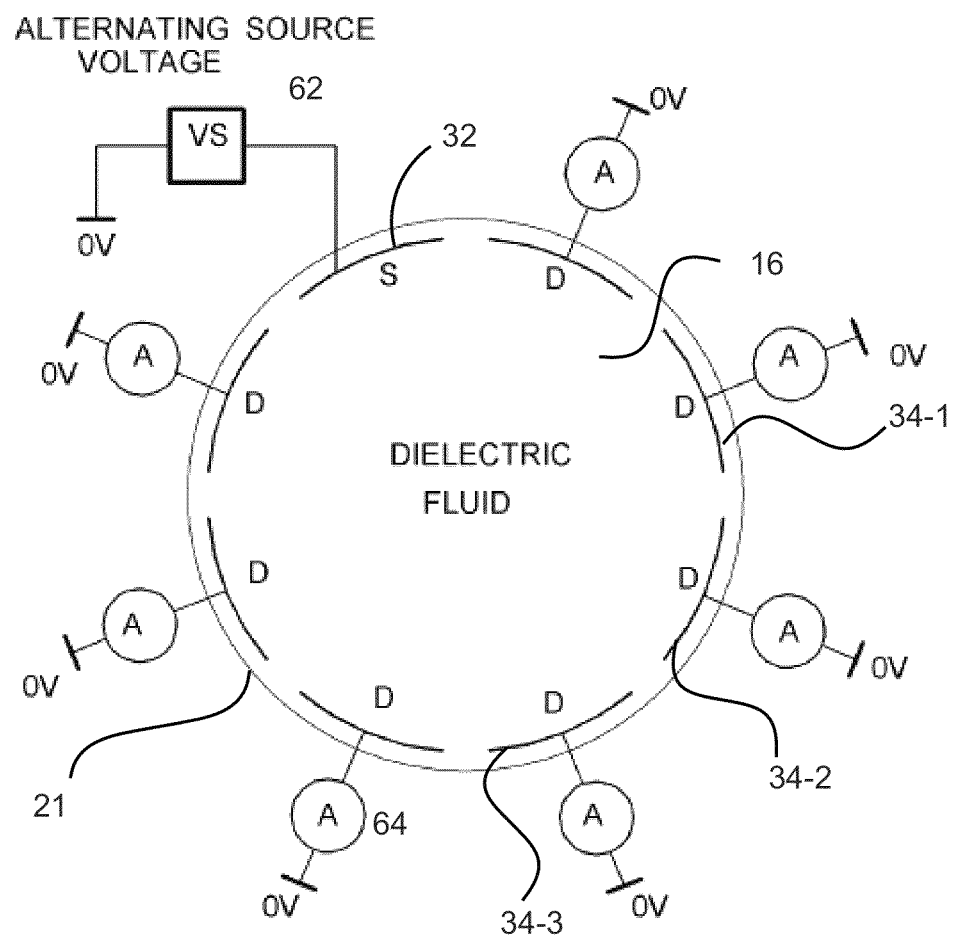
FIG. 2 shows a capacitance measurement principle.
Figure 2:
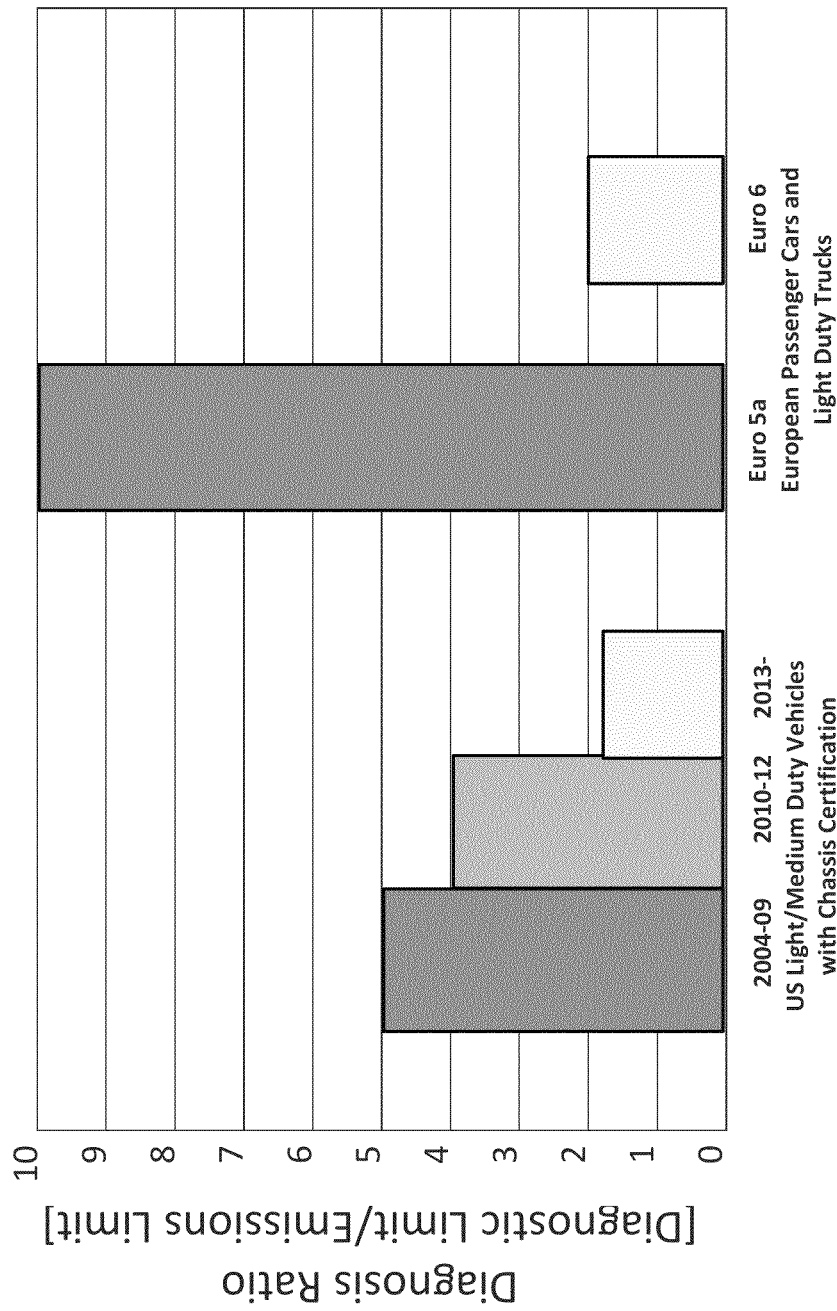

However, as the PM or soot is retained by the filter, the filter passageway increasingly becomes more restrictive resulting in elevated back pressure in the exhaust. This further results in lower fuel efficiency for the engines since the pistons have to exert more pressure to purge the exhaust gas. One effective way to address this problem is to burn the soot load in the DPF periodically either by injecting more fuel in the engine or by a separate combustor upstream of the DPF with the aid of a diesel oxidation catalyst (DOC). The latter which is known as active regeneration of DPF is more efficient and is commonly used for DPF. Here a fuel doser is used to raise the exhaust gas temperature to burn off the soot load in DPF. The timing and amount of fuel dosing is critical in ensuring optimal performance of DPF functions. Current DPF particulate matter detection methods are not likely to be suitable for meeting the stricter requirements as seen in FIG. 2-2.

The performance efficiency of a DPF with active regeneration is largely dependent on the accuracy of soot load estimation. Current soot load estimation is based on differential pressure measurement across the DPF whose accuracy can vary up to 50% from the true soot load. As a result, fuel dosing for active regeneration may not be optimal. It has been shown that fuel penalty caused by regeneration (2.2% to 5.3%) is more than fuel penalty due to backpressure (1.5% to 2.0%). Accurate soot load knowledge is also necessary if one wants to rule out possible overheating of the DPF caused by exothermic soot oxidation. Because if DPF is allowed to accumulate too much particulate matter, the large amount of heat released upon regeneration cannot effectively be dissipated, resulting filter damage such as by the formation of cracks or regions which may be locally melted.

The knowledge of the tomography of DPF can help minimize the impact of fuel consumption and avoid damaging the filter and other after treatment systems. Various embodiments of the present invention pertain to a novel instantaneous soot load sensor based on electrical capacitance that can improve the soot load estimation. This sensor can be used in the feedback loop to improve the soot load estimation allowing for correct amount of fuel injection upstream of diesel oxidation catalyst (DOC) and thus potentially improving the overall DPF performance. Various embodiments discussed herein pertain to the designing, building, and implementing a feedback control system for an actively regenerated DPF based on real-time electrical capacitance soot load sensor feedback and presented it here for the first time.

Various embodiments of the present invention pertain to the designing, building, and implementation of long range predictive feedback control system with parameter adaptation for an actively regenerated Diesel Particulate Filter (DPF) in order to improve fuel efficiency of regeneration process as well as the engine. Still other embodiments provide improved diagnostics capability for the DPF to the On Board Diagnostic (OBD) system. Although what will be shown and described are aspects pertaining to diesel engine particulate filters, it is understood that the various apparatus, methods, and ideas presented herein are further applicable to various types of filters (including those that filter liquid or gaseous media), as well as to various application (including exhaust filters for any kind of engine, as well as filters for power plants and industrial processes).

Various embodiments include apparatus and methods that improve overall fuel and PM filtering efficiency and durability of a DPF by a novel closed-loop active regeneration system and controller using electrical capacitance based soot load sensing technology. In still further embodiments the overall fuel efficiency of the diesel engine can be improved by up to 2% through the developed technology in the proposed project.

One embodiment includes a diesel after-treatment system including Diesel Oxidation Catalyst (DOC)/DPF with an estimation of soot load as an output and an amount of fuel dosing as an input, along with a dynamic model for electrical capacitance based soot load sensor. It further includes a feedback control system for active DPF regeneration for optimal performance. The developed models are integrated with the controller model for simulation purposes, although in some embodiments portions of these models (including simplifications of the models) may be used for control purposes.

One embodiment includes an electronic controller that can implement closed loop control of an actively regenerated diesel particulate filter (DPF) based on instantaneous feedback from an electrical capacitance tomography based soot loading sensor responsive to the overall DPF performance efficiency. Thus an appropriate closed loop control whose inputs are accurate activates regeneration mode just when it is required. An instantaneous soot load sensor based on electrical capacitance can improve the soot load estimation. Various embodiments employ this sensor in the feedback loop to improve the soot load estimation allowing for correct amount of fuel injection upstream of diesel oxidation catalyst (DOC) and thus potentially improving the overall DPF performance. This sensor can be utilized in a feedback control system for an actively regenerated DPF based on real-time electrical capacitance soot load sensor feedback.

Since the DPF's filtering characteristics (e.g. porosity, flow resistance and effective volume) are subject to change over time due to ash accumulation and regeneration hysteresis, it becomes helpful to adapt the controller parameters based on these changes for optimal performance. In order to provide DPF performance without degradation, an adaptive control system for the closed loop DPF is further included in yet other embodiments. Still further embodiments include a long range predictive control algorithm to further enhance the estimates of soot deposits in DPF many time steps ahead and use this estimate for optimal active regeneration. The predictive control algorithm is aimed at compensating for the system dead times by taking control action at current time based on future estimates and thus providing improved overall system performance.

One embodiment of the sensor includes two parallel plates of a conducting material separated by an air gap connected through a switch and a resistor to a battery for simple measurement of the soot state of the DPF. It is further understood that these plates can likewise interface with voltage drivers and voltage measurement devices of a computer as disclosed herein and in various embodiments. If the parallel plates are initially uncharged and the switch is left open, no net positive or negative charge will exist on either plate. The instant the switch is closed. However, electrons are drawn from the upper plate through the resistor to the positive terminal of the battery. There will be a surge of current at first, limited in magnitude by the resistance present. The level of flow will then decline, as will be demonstrated in the sections to follow. This action creates a net positive charge on the top plate. Electrons are being repelled by the negative terminal through the lower conductor to the bottom plate at the same rate they are being drawn to the positive terminal. This transfer of electrons continues until the potential difference across the parallel plates is exactly equal to the battery voltage. The final result is a net positive charge on the top plate and a negative charge on the bottom plate.

This element, constructed of two parallel conducting plates separated by an insulating material (air, sand etc.), operates as a capacitor. If a potential difference of V volts is applied across the two plates separated by a distance of d, the electric field strength between the plates is determined by $$E = V/d$$

The ratio of the flux density to the electric field intensity in the dielectric is called the permittivity of the dielectric $$\in = D/E$$

For a vacuum, the value of $\in$ (denoted by $E_o$) is $8.85*10^{-12}$ F/rn. The ratio of the permittivity of any dielectric to that of a vacuum is called the relative permittivity. It simply compares the permittivity of the dielectric to that of air. In equation form $$\varepsilon r = \frac{\varepsilon}{\varepsilon o}$$

$$\varepsilon = \frac{D}{E} = \frac{\frac{Q}{A}}{\frac{V}{d}} = \frac{Qd}{VA}$$

Again $C = \frac{Q}{V}$

Therefore $\varepsilon = \frac{Cd}{A}$ $$C = \varepsilon \frac{A}{d}$$

Or, $C = \varepsilon o \varepsilon r \frac{A}{d}$

Figures 2, 3:
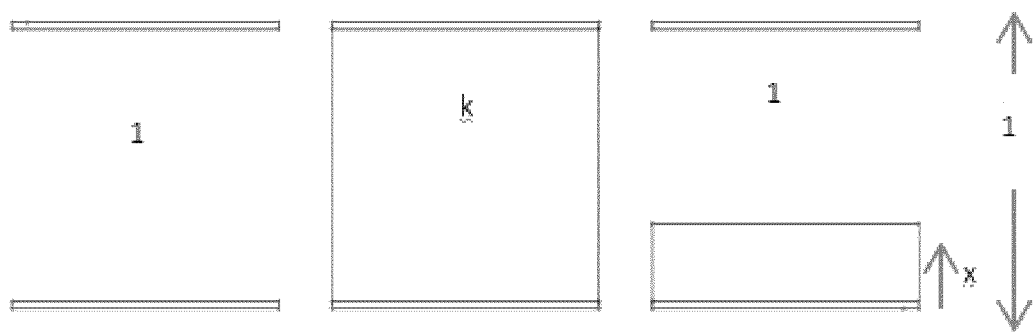
FIG. 3 shows an ECT in DPF.

If two components in the filter pipe lie on top of one another, the effective capacitance can be considered as two capacitances connected in series. This is illustrated in FIG. 2-3. In this case, the capacitance and permittivity are related in a nonlinear fashion. The effective permittivity and overall capacitance is given respectively in equation (5) and equation (6).

$$\varepsilon_s = \frac{\varepsilon_r \varepsilon_0 x(1-x)}{1-x(\varepsilon_r - 1)} \quad (5)$$

$$C_s = \frac{A\varepsilon_s}{d} \quad (6)$$

Figures 2, 3, 4:
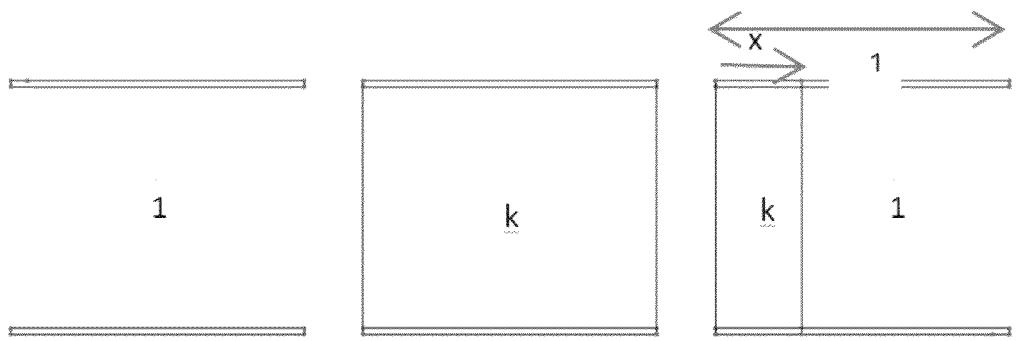
Figures 2, 3, 4, 5, 6, 7:
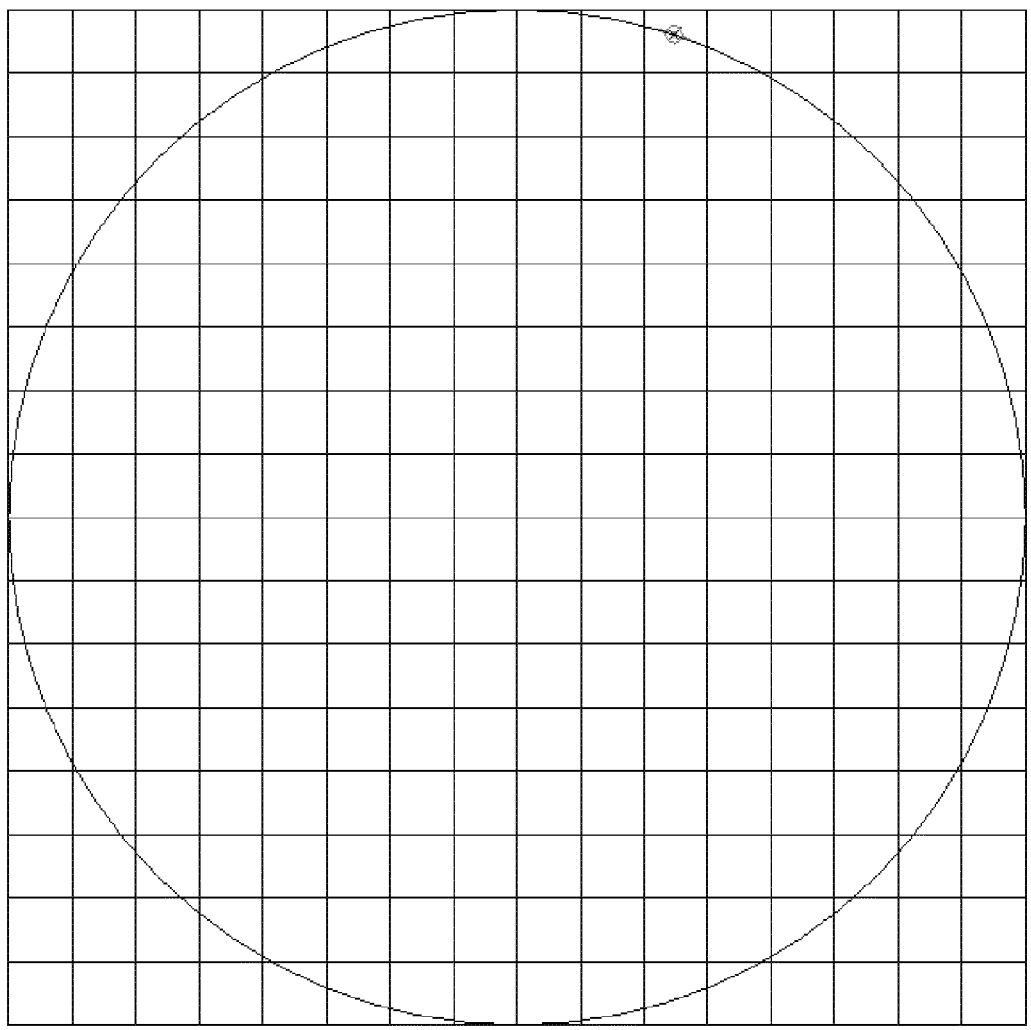

If two components in the pipe appear as discrete band and appear side by side, their effective capacitance can be considered as two capacitances connected in parallel. This is illustrated in FIG. 2-4. In this case, the capacitance and permittivity are related linearly. The effective permittivity and overall capacitance is given respectively in equation (7) and equation (8).

$$\varepsilon_p = \varepsilon_o[1 + x(\varepsilon_r - 1)] \quad (7)$$

$$C_p = \frac{A\varepsilon_p}{d} \quad (8)$$

The generalized Maxwell Garnett mixing formula for multiphase mixtures with randomly oriented ellipsoidal inclusions in equation (9) and equation (10).

$$\varepsilon_m = \varepsilon_b + \frac{\frac{1}{3}\sum_{i=1}^{n} f_i(\varepsilon_i - \varepsilon_b)\sum_{k=1}^{3} \frac{\varepsilon_b}{\varepsilon_b + N_{ik}(\varepsilon_b - \varepsilon_b)}}{1 - \frac{1}{3}\sum_{i=1}^{n} f_i(\varepsilon_i - \varepsilon_b)\sum_{k=1}^{3} \frac{\varepsilon_b}{\varepsilon_b + N_{ik}(\varepsilon_b - \varepsilon_b)}} \quad (9)$$

$$C_r = \frac{A\varepsilon_m}{d} \quad (10)$$

Where
$\varepsilon_b$=relative permittivity of a base dielectric
$\varepsilon_i$=relative permittivity of the i-th sort of inclusions
$F_i$=volume fraction occupied by the inclusions of the i-th sort
$N_{ik}$=depolarization factors of the i-th sort of inclusions
Index k=1, 2, 3 corresponds to x, y, and z Cartesian coordinates.

Based on the above mentioned principles, electrical capacitance tomography (ECT) system according to one embodiment can be established. ECT is used to obtain information about the spatial distribution of a mixture of dielectric materials inside a vessel, by measuring the electrical capacitances between sets of electrodes placed around its periphery and converting these measurements into an image, graph, or data set suitable for display to an operator or as an input to a control system showing the distribution of permittivity. The images are approximate, but can be generated at relatively high speeds.

ECT can be used with any arbitrary mixture of different non-conducting dielectric materials, such as plastics, hydrocarbons, sand or glass, as examples. One application of ECT is viewing and measuring the spatial distribution of a mixture of two different dielectric materials (a two-phase mixture), and in some embodiments, the concentration distribution of the two components over the cross-section of the vessel which can be obtained from the permittivity distribution. An ECT system in one embodiment includes a capacitance sensor, Capacitance Measurement Unit (CMU) and a control computer. For imaging a single vessel type with a fixed cross-section and with a fixed electrode configuration, the measurement circuitry can be integrated into the sensor and the measurement circuits can be connected directly to the sensor electrodes.

An ECT system in one embodiment includes a capacitance sensor, a Capacitance Measurement Unit (CMU), and a control computer. For imaging a single vessel type with a fixed cross-section and with a fixed electrode configuration, the measurement circuitry can be integrated into the sensor and the measurement circuits can be connected directly to the sensor electrodes. This simplifies the measurement of inter-electrode capacitances and is useful for standardized industrial sensors.

In some applications for ECT it is preferable to have a standard capacitance measuring unit which can be used with a wide range of sensors. In this case, screened cables preferably connect the sensor to the measurement circuitry, which should be able to measure very small inter-electrode capacitances, of the order of 10-15 F (1 femtofarads fF), in the presence of much larger capacitances to earth of the order of 200,000 fF (mainly due to the screened cables). A diagram of a basic ECT system of one type is shown in FIG. 1.

An ECT system according to one embodiment includes a set of capacitor plates placed around a pipe or other vessel including a filter. A source voltage is applied between one electrode (the source electrode) and ground and the resulting currents flow between the source electrode and the remaining (detector) electrodes to ground are measured. These currents are directly proportional to the capacitances between the source and detector electrodes.

An ECT in some embodiments includes a set of measurement projections made by exciting each electrode in turn as a source electrode and measuring the currents which flow into the remaining detector electrodes. So for an 8-electrode sensor, there will be 8×7=56 possible capacitance measurements. However, as half of these will be reciprocal measurements (the same capacitance should be measured by exciting electrode 1 as a source and measuring the current into electrode 2 as is obtained by exciting electrode 2 as a source and measuring the current into electrode 1 etc.), there could be 28 unique capacitance measurements for a complete set of projections. In general for a sensor with E electrodes, there will be E(E−1)/2 unique capacitance measurements.

The set of measured inter-electrode capacitance values and subsequently obtained permittivity's are normalized to construct the permittivity images.

$$\text{Capacitance normalize, } C_n = \frac{C_i - C_i(emp)}{C_i(\text{full}) - C_i(emp)} \quad 0 < C_n < 1$$

$$\text{Permittivity normalize, } K_n = \frac{Ki - Ki(emp)}{Ki(\text{full}) - Ki(emp)} \quad 0 < K_n < 1$$

The normalized values are then projected into a square pixel grid where the pixel values are similarly normalized to lie between 0 to 1. The image formed is an approximate solution.

The permittivity image or tomographic images are mapped onto a square pixel grid, which are also normalized, so that these pixel values have the values ranged from 0 to 1. The complete set of a measured inter-electrode capacitance values is required to reconstruct one permittivity distribution image. FIG. 2-7 shows a 16*16 square pixel grid used to display the permittivity distribution image of a 4-electrode sensor having circular intersection of Diesel particulate filter. From this (16*16) square pixel grid containing 256 pixels, only 210 (approx.) are needed to construct the cross sectional image of the DPF and remaining pixels are not required and hence neglected. The field lines between two plates are curved and to suit the requirement these lines can be approximated.

A simple procedure for reconstructing an image of an unknown permittivity distribution inside the sensor from the capacitance measurements is the Linear Back Projection (LBP) algorithm. LBP has the advantage of being quite fast, in practice requiring only the multiplication of a fixed reconstruction matrix times the vector of measurements.

Consider an x-electrode sensor and square pixel grid pixel number is N. A grey level K(N) for each pixel has been calculated by the basic LBP formula.

$$K(N) = \frac{\sum_{i=0}^{m} C_i S_i(N)}{\sum_{i=0}^{m} S_i(N)} \quad (11)$$

Numerator in equation (11) shows actual back projection operation whereas denominator serves as a position dependent weighting factor used to compensate for the decrease in sensitivity towards the center of the sensor.

The forward transform relationship between capacitance permittivity distributions can be approximated and written in a normalized form as:

$$[C]=[S][K] \quad (12)$$

[C]=M×1 matrix containing the normalized electrode-pair capacitances Cm (in the nominal range 0 to 1).

[K]=N×1 matrix containing the normalized pixel permittivity's (in the nominal range 0 to 1) N is the number of pixels representing the sensor cross-section.

[S]=M×N matrix containing the set of sensitivity matrices for each electrode-pair. This sensitivity map can be defined as $$S_i(N) = \frac{C_i(N) - C_i(emp)}{C_i(\text{full}) - C_i(emp)} \text{ For } i = 1...M.$$

The sensitivity matrix describes how the measured capacitance between any combinations of electrodes changes when a change is made to the dielectric constant of a single pixel inside the sensor. The properties of the capacitance sensor are measured or calculated initially to produce a sensor sensitivity matrix for the case when the sensor is empty. This matrix is a composed of a set of sub-matrices (or maps) whose elements correspond to the individual pixels in a rectangular grid which is used to define the sensor cross section. The sensor is normally calibrated at each end of the range of permittivity's to be measured by filling the sensor with the lower permittivity material initially and measuring all of the individual inter-electrode capacitances. This operation is then repeated using the higher permittivity material. The data obtained during the calibration procedure is used to set up the measurement parameters for each measuring channel and is stored in a calibration data file.

In principle, once the set of inter-electrode capacitances C have been measured, the permittivity distribution K can be obtained from these measurements using an inverse transform Q as follows in equation (13).

$$[K]=[Q][C] \quad (13)$$

From previous [C] and [K] relationship it's visible that Q is simply the inverse of the matrix S matrix with dimensions (N×M). However, it is not possible to find the true inverse of a non-square matrix (where M≠N) so physically it is not possible to obtain the individual values of a large number of pixels (e.g. 256) from a smaller number of capacitance measurements (e.g. 28).

Direct contributions of pixels to the measured capacitance between any specific electrode-pair is not be specified, but it can be shown from the sensitivity matrix S that certain pixels have more effect than others on this capacitance. Consequently, component values allocated to each pixel proportional to the product of the electrode-pair capacitance and the pixel sensitivity coefficient for this electrode-pair. Based on this approximation the LBP algorithm uses the transpose of the sensitivity matrix, [S'] an approximate matrix which has the dimensions (N×M) so that [S']=[Q].

This process is repeated for each electrode-pair capacitance in turn and the component values obtained for each pixel are summed for the complete range of electrode-pairs.

Testing has been accomplished with an ECT including an experimental model of DPF made of Nylon 66. This nylon 66 has very close dielectric properties of conventional DPF made from cordierite which has dielectric property of 4.7 (approx.) in 1 MHz.

The DPF outer shell wall is conductive and the ECT system electrode is placed inside of the DPF wall. In that case the components of capacitance due to the electric field inside the sensor should increase in proportion to the material permittivity when a higher permittivity material is introduced inside the sensor.

The internal temperature of DPF will be highest when the regeneration of soot is taking place. Regeneration is a process of soot removal from the DPF, including approaches that are active or passive. Active systems use extra fuel, whether through burning to heat the DPF, or providing extra power to the DPF's electrical system. This process required 600° C. to burn Diesel particulate matter. This temperature can be reduced to somewhere in the range of 350° C. to 450° C. by use of a fuel borne catalyst. One way to burn soot at lower temperature is known as Johnson Matthey's two-component design. In this approach the catalyst is positioned before the filter to convert NO into $NO_2$. The $NO_2$ then oxidizes the soot that is collected on the filter to regenerate the filter. The soot is combusted at a much lower temperature than is normally required. In fact, the CRT continuously regenerating technology enables the filter to be regenerated at a temperature that is 20% lower than other filters on the market. By using this approach the soot burning temperature can be reduced up to 240° C. So whatever material we are using as ECT electrode should be able to withstand a versatile range of temperature. One embodiment includes copper as the ECT electrode:
1) Melting point at 1357° K or 1084° C.
2) Does not react with water
3) Resistivity=$1.68*10^{-8}$ (Ω·m) at 20° C.
4) Conductivity=$5.96*10^{-7}$ S/m) at 20° C.
5) Temperature coefficient=$0.003862(K^{-1})$
6) Copper resists corrosion from moisture, humidity and industrial pollution
7) However products from other carrion like oxide, chloride and sulfide are conductive.

Due to very low temperature coefficient of copper the change of conductivity with the change of temperature will be very low. If the assumption made that the temperature change inside of DPF is linear then relationship between resistivity and temperature will be $$\rho(T)=\rho_0[1+\alpha(T-T_0)] \quad (14)$$

where $T_0$ is the room temperature. If the temperature T become 300° C. then $$\rho(T)=1.68*10^{-8}[1+0.003862(300-20)]$$

$$\rho(T)=3.49*10^{-8}(\Omega\cdot m)$$

FIG. 3 shows an isometric view of the experimental setup with 8 capacitance electrodes and DPF model of 152 mm (6 in) length with 130 mm (5 in) diameter. There is a trade-off has to be done to choose the number of electrode. Higher number of electrodes means complicated and expensive data acquisition hardware, smaller capacitance to be measured; slower data acquisition as we can see from Table 1 and currently 8-12 numbers of electrodes are commonly used in an ECT sensor, as one example. These 8 electrodes are placed around the DPF.

Figures 2, 3, 4, 5, 6, 7, 8, 9:
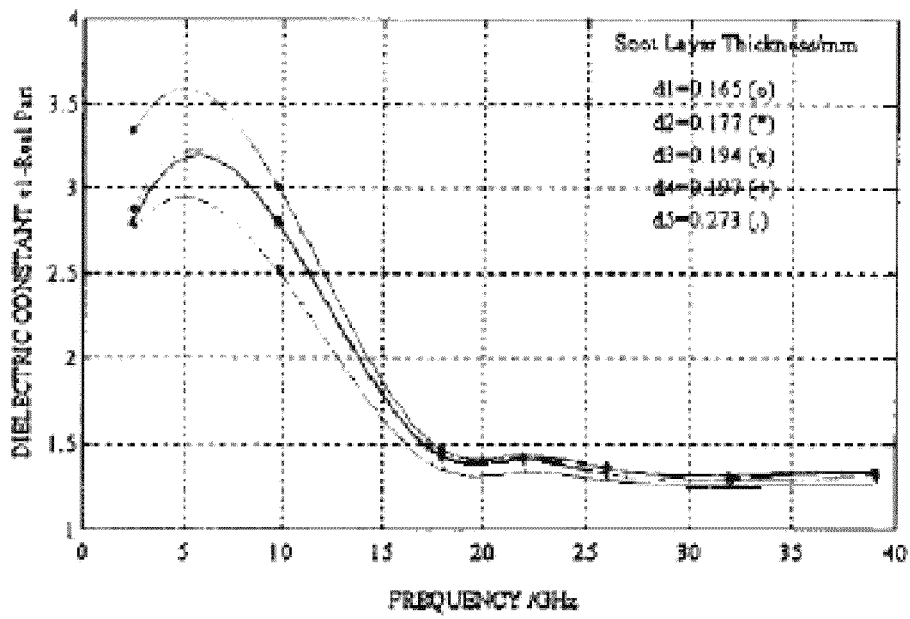
Figures 2, 3, 4, 5, 6, 7, 8, 9, 10:
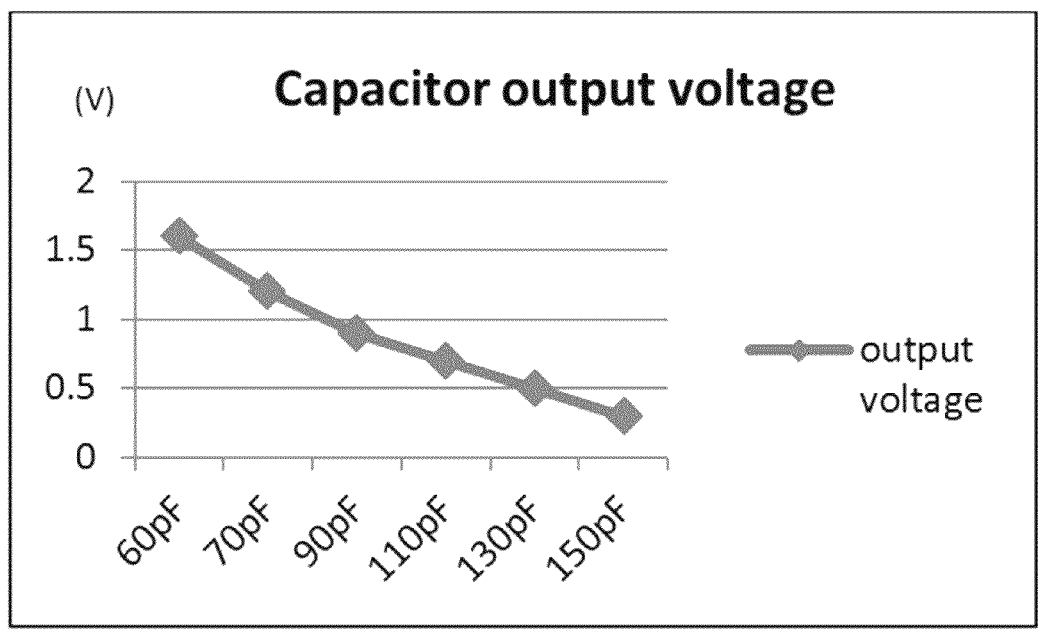
Figures 2, 3, 4, 5, 6, 7, 8, 9, 10, 11:
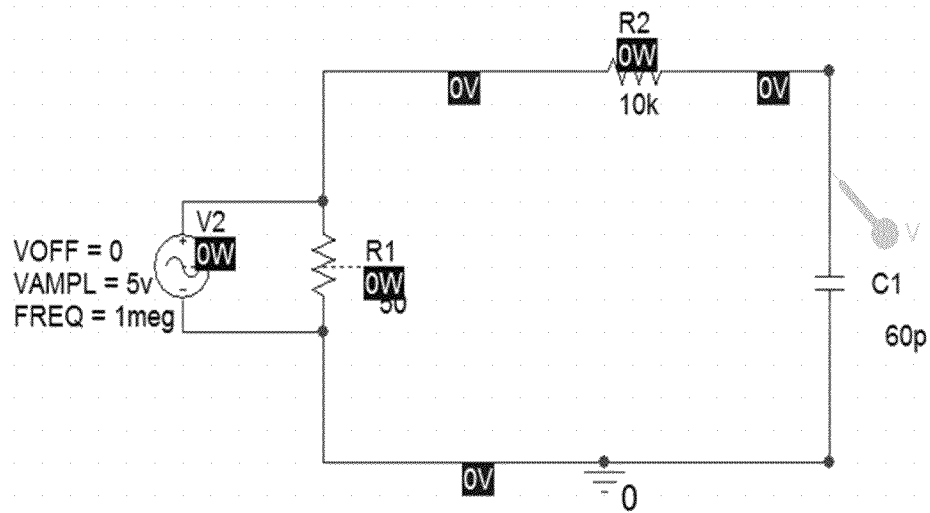
Figures 2, 3, 4, 5, 6, 7, 8, 9, 10, 11, 12:
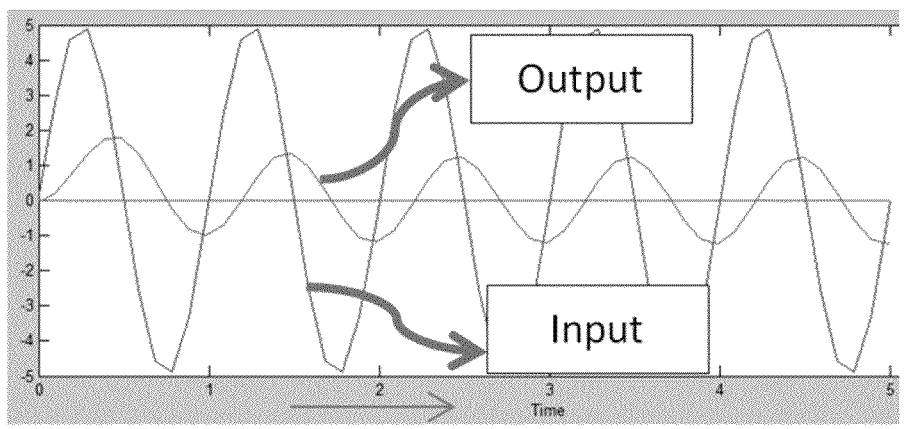
Figures 2, 3, 4, 5, 6, 7, 8, 9, 10, 11, 12, 13:
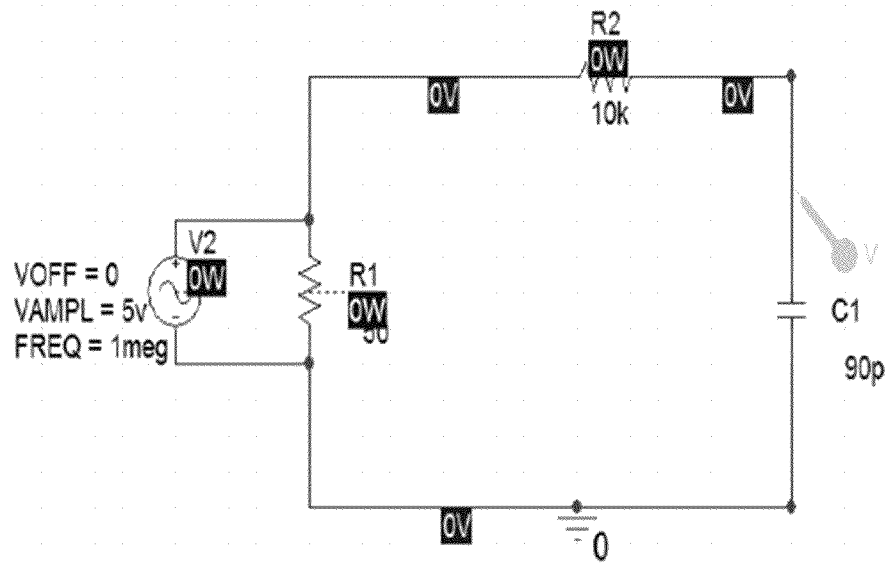
Figures 2, 3, 4, 5, 6, 7, 8, 9, 10, 11, 12, 13, 14:
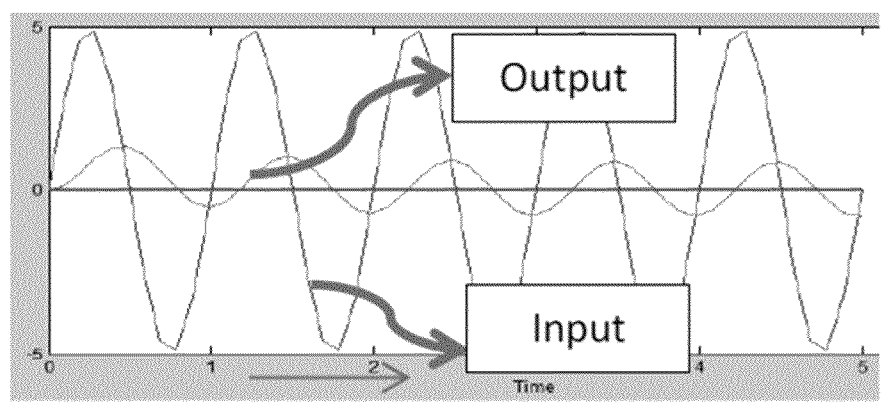
Figures 2, 3, 4, 5, 6, 7, 8, 9, 10, 11, 12, 13, 14, 15:
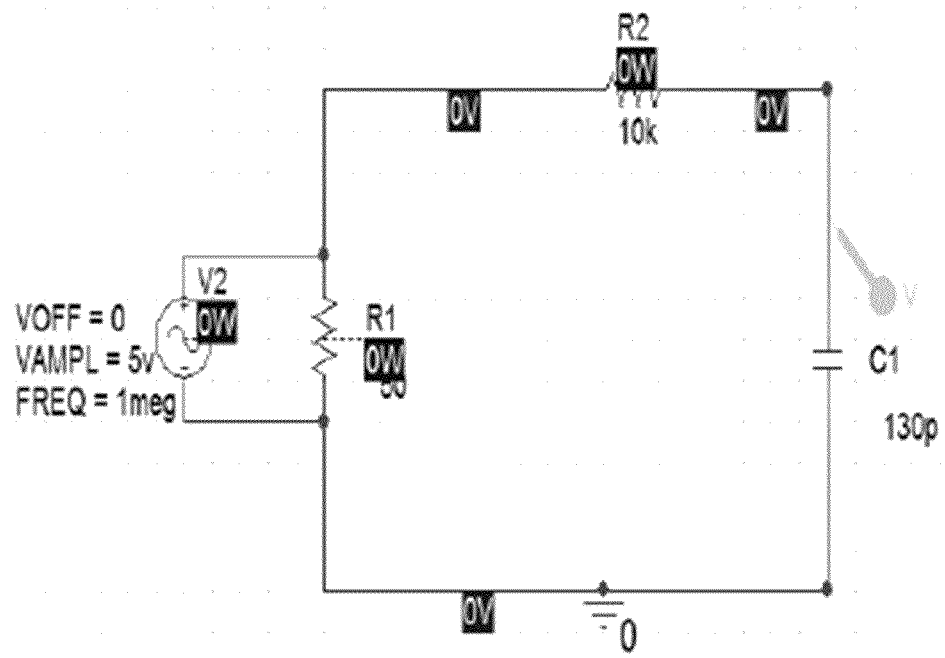
Figures 2, 3, 4, 5, 6, 7, 8, 9, 10, 11, 12, 13, 14, 15, 16:
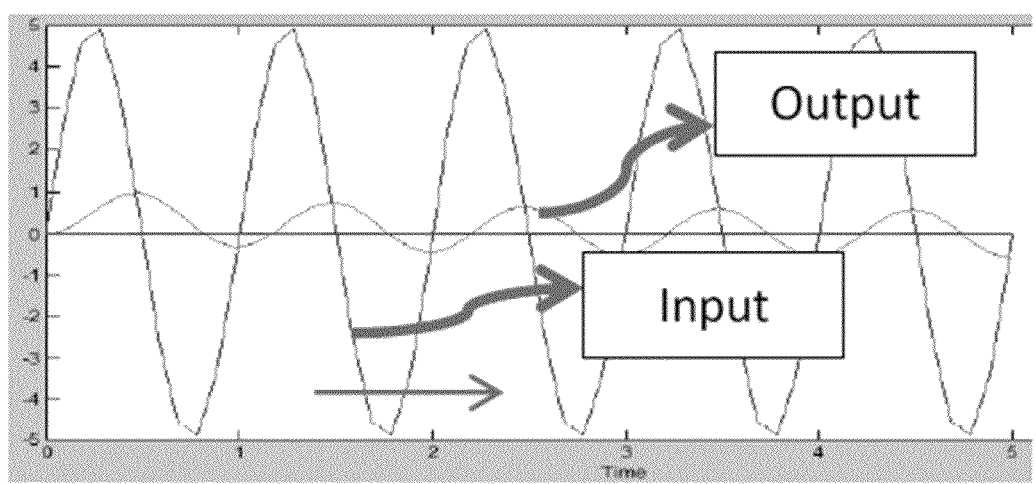
Figures 2, 3, 4, 5, 6, 7, 8, 9, 10, 11, 12, 13, 14, 15, 16, 17, 17A:
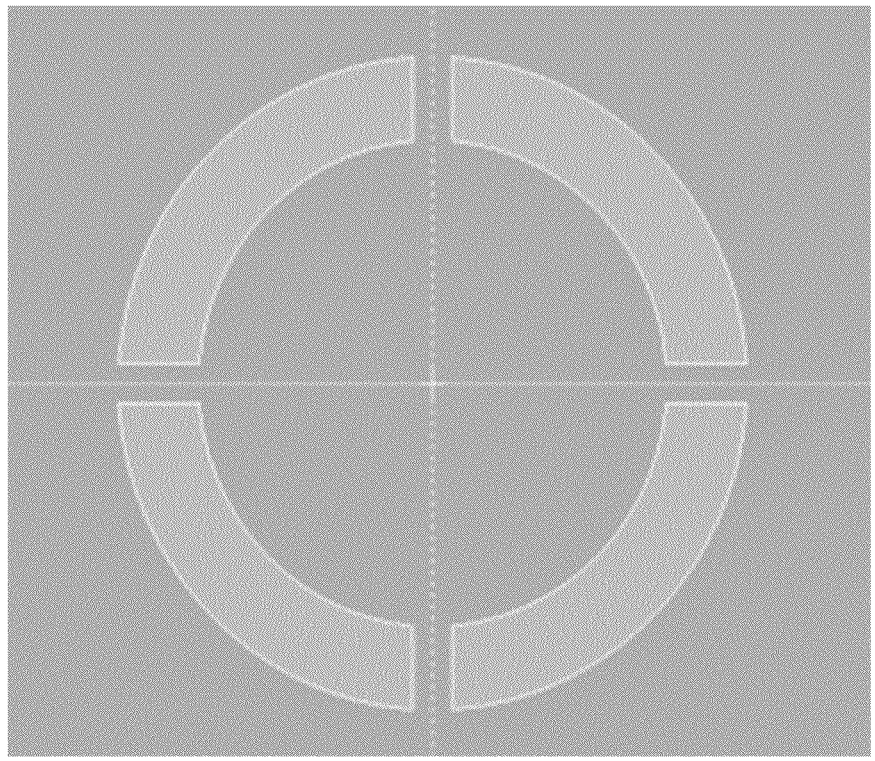
Figures 2, 3, 4, 5, 6, 7, 8, 9, 10, 11, 12, 13, 14, 15, 16, 17, 17B:
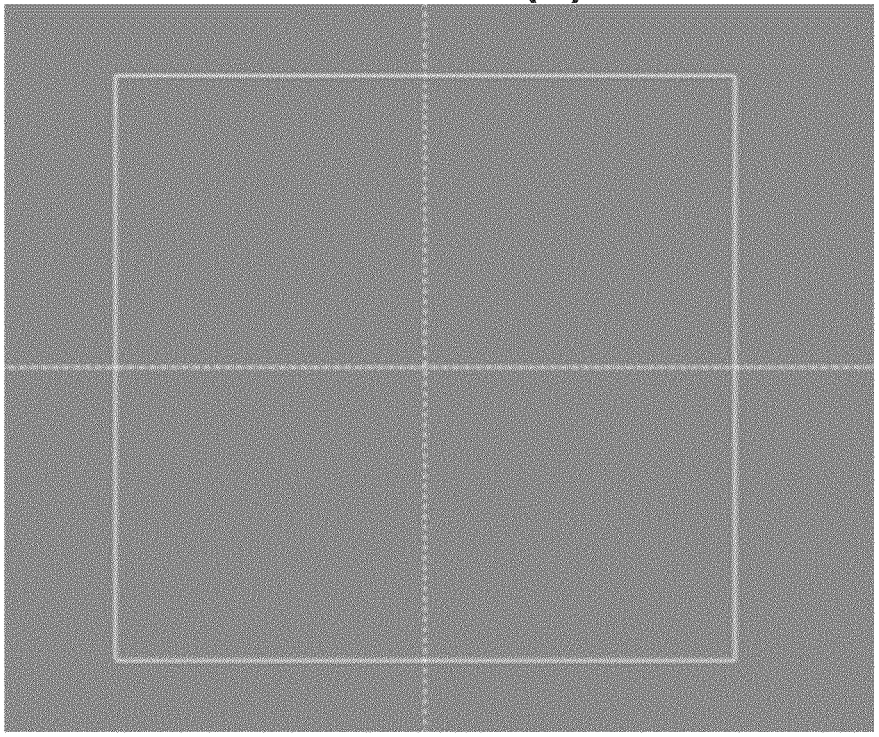
Figures 2, 3, 4, 5, 6, 7, 8, 9, 10, 11, 12, 13, 14, 15, 16, 17, 18:
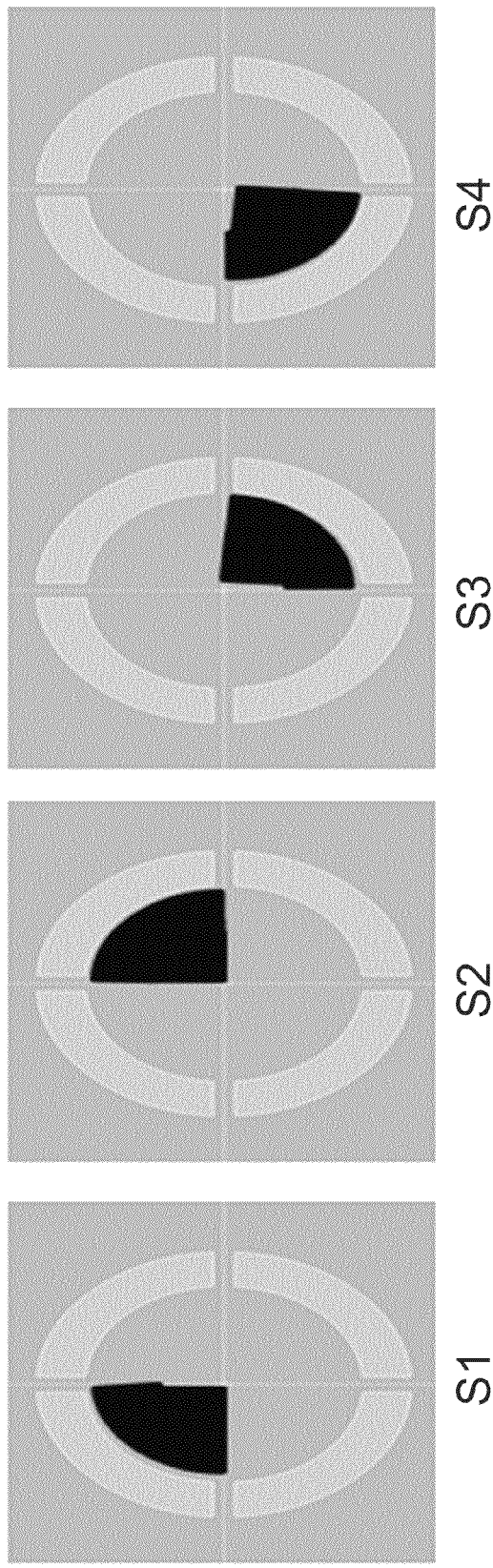
Figures 2, 3, 4, 5, 6, 7, 8, 9, 10, 11, 12, 13, 14, 15, 16, 17, 18, 19:
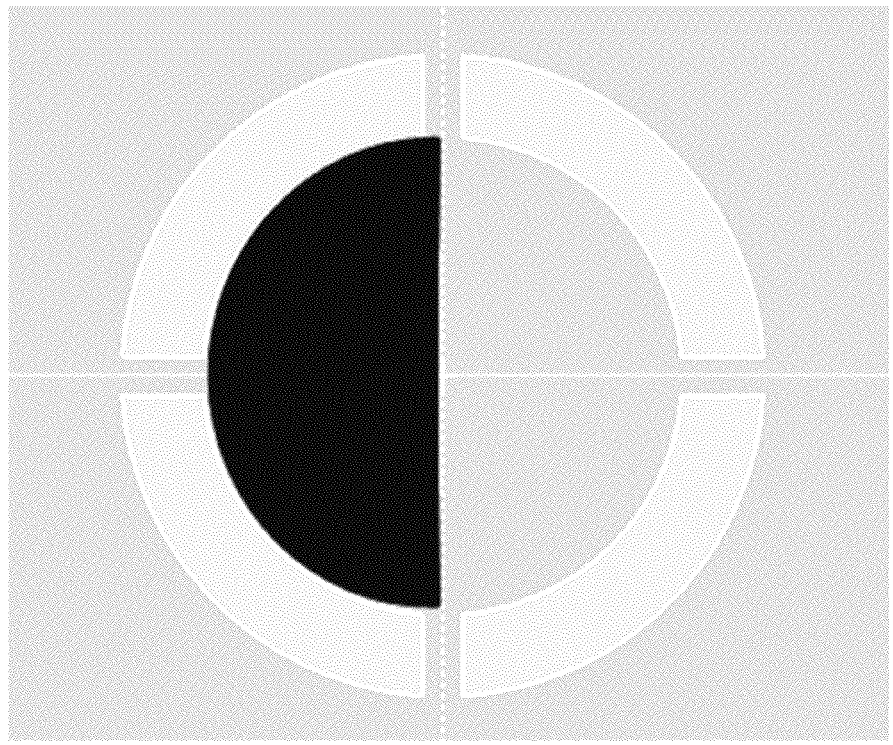
Figures 2, 3, 4, 5, 6, 7, 8, 9, 10, 11, 12, 13, 14, 15, 16, 17, 18, 19, 20:
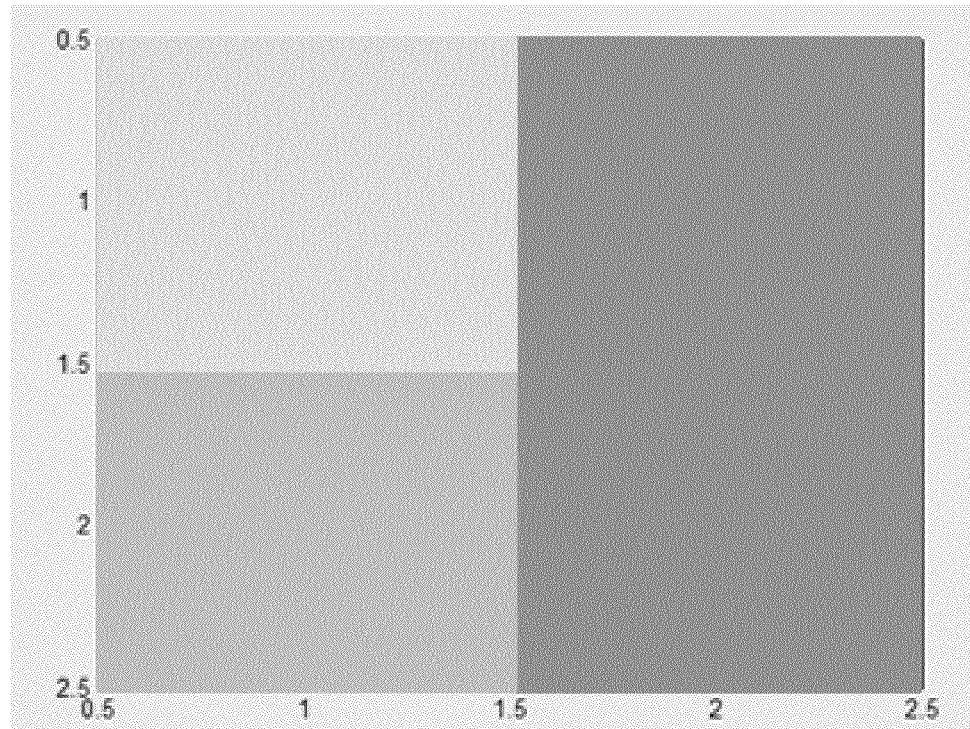
Figure 3:
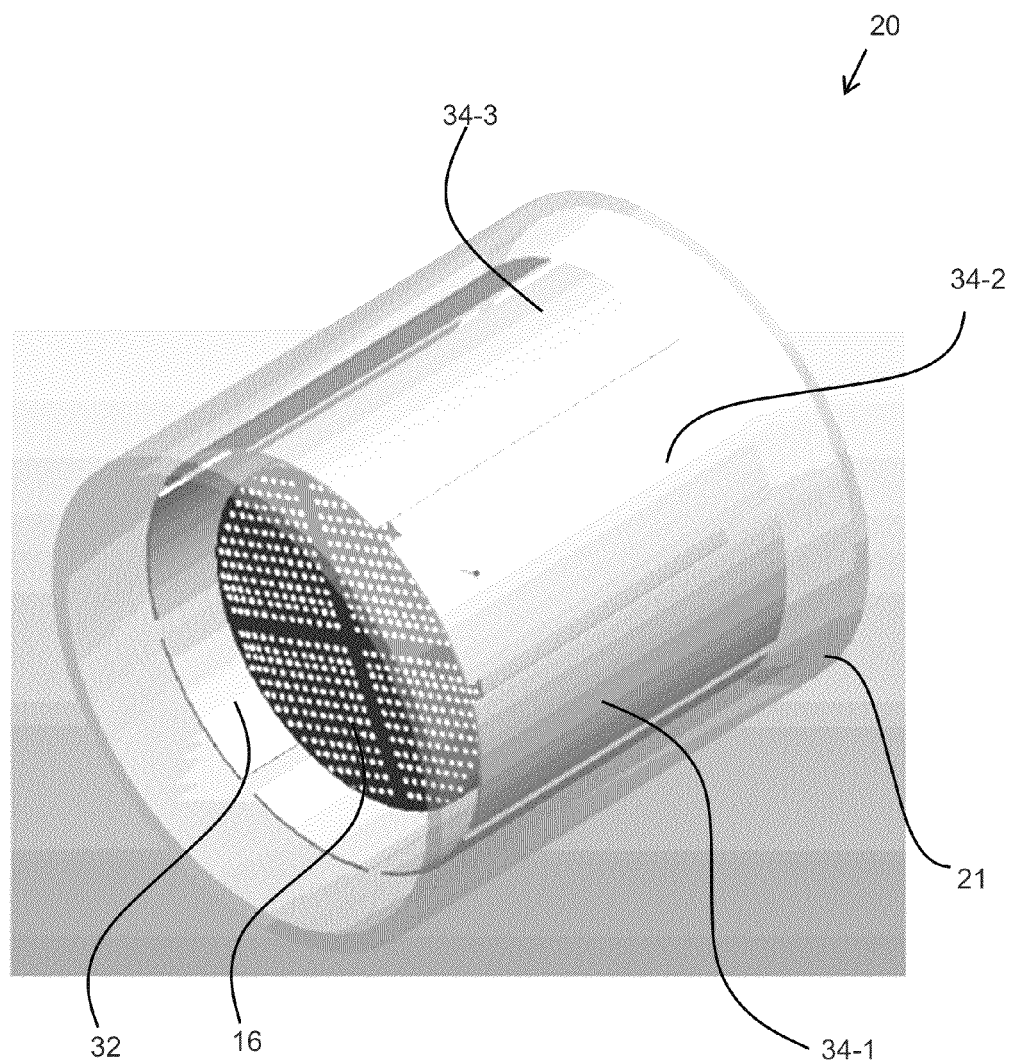
Figure 4A:
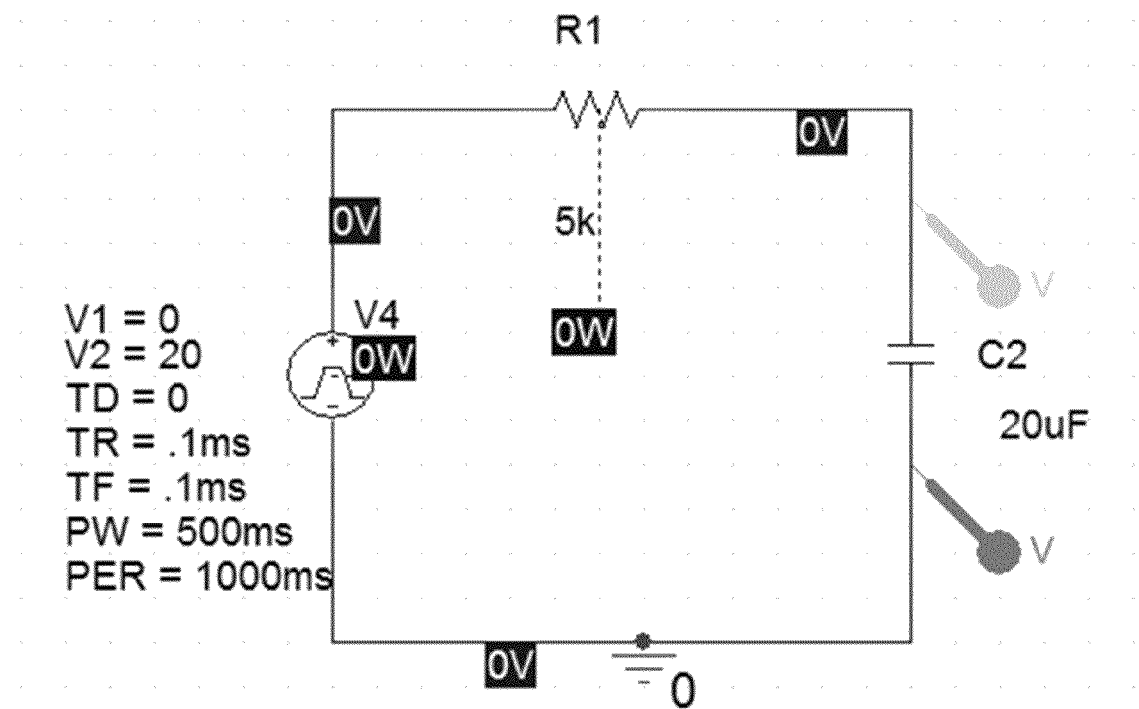
FIG. 4A shows a 20 uF capacitor measurement circuit.
Figure 4B:
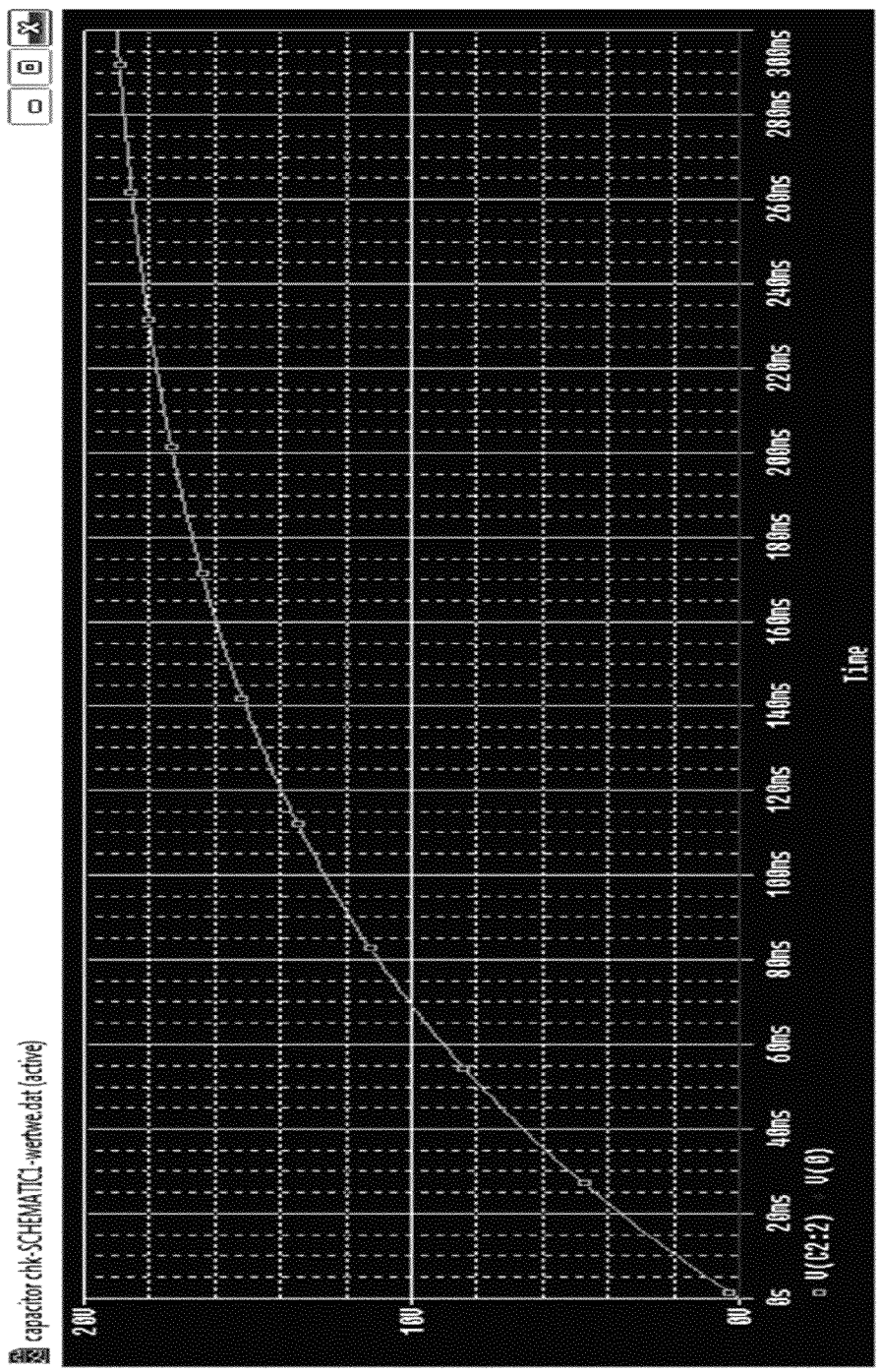
FIG. 4B is a graphical representation of FIG. 4A.
Figure 5A:
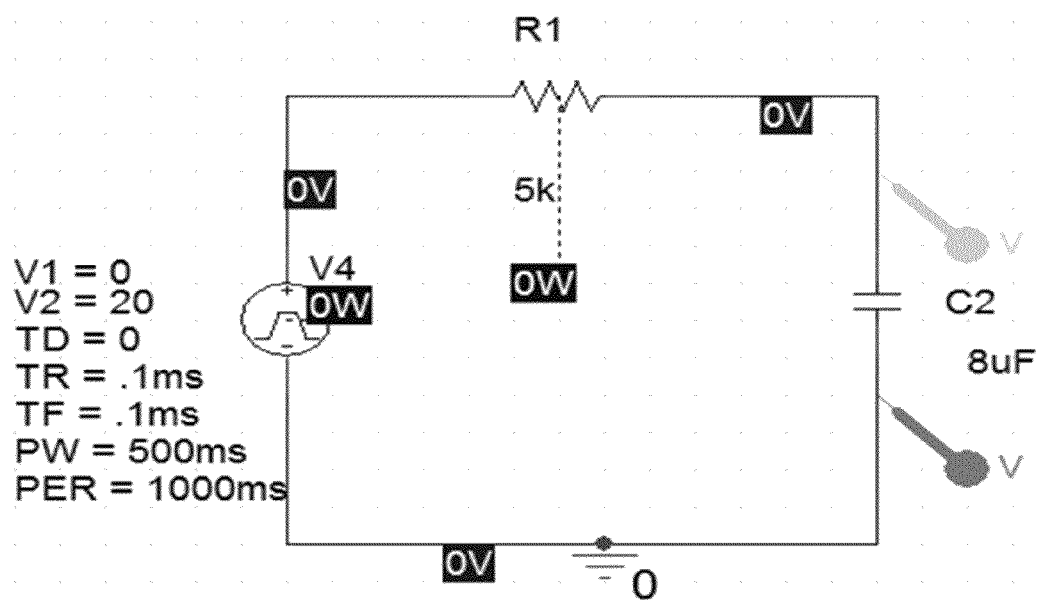
FIG. 5A shows 8 uF capacitor measurement circuit.
Figure 5B:
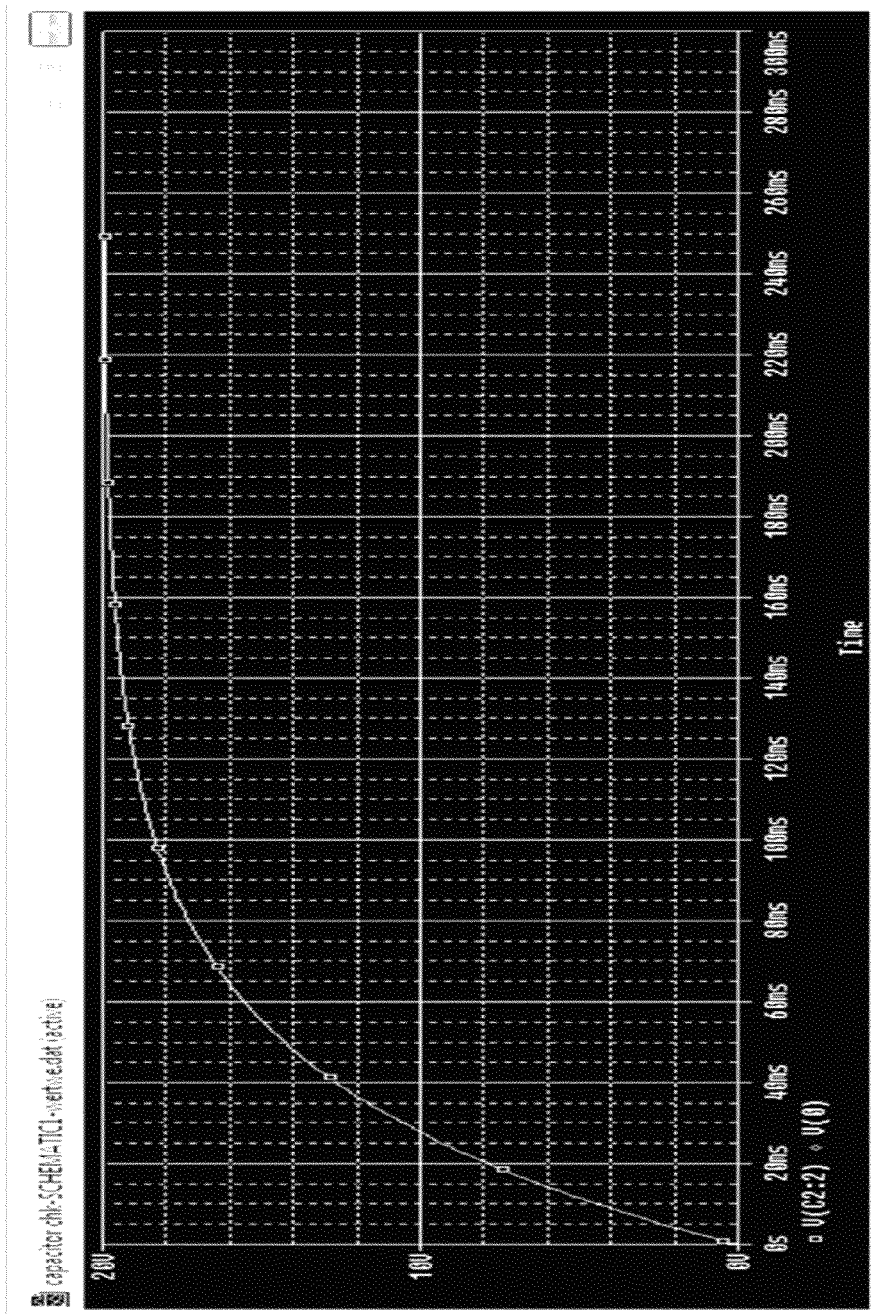
FIG. 5B is a graphical representation of FIG. 5A.
Figure 6A:
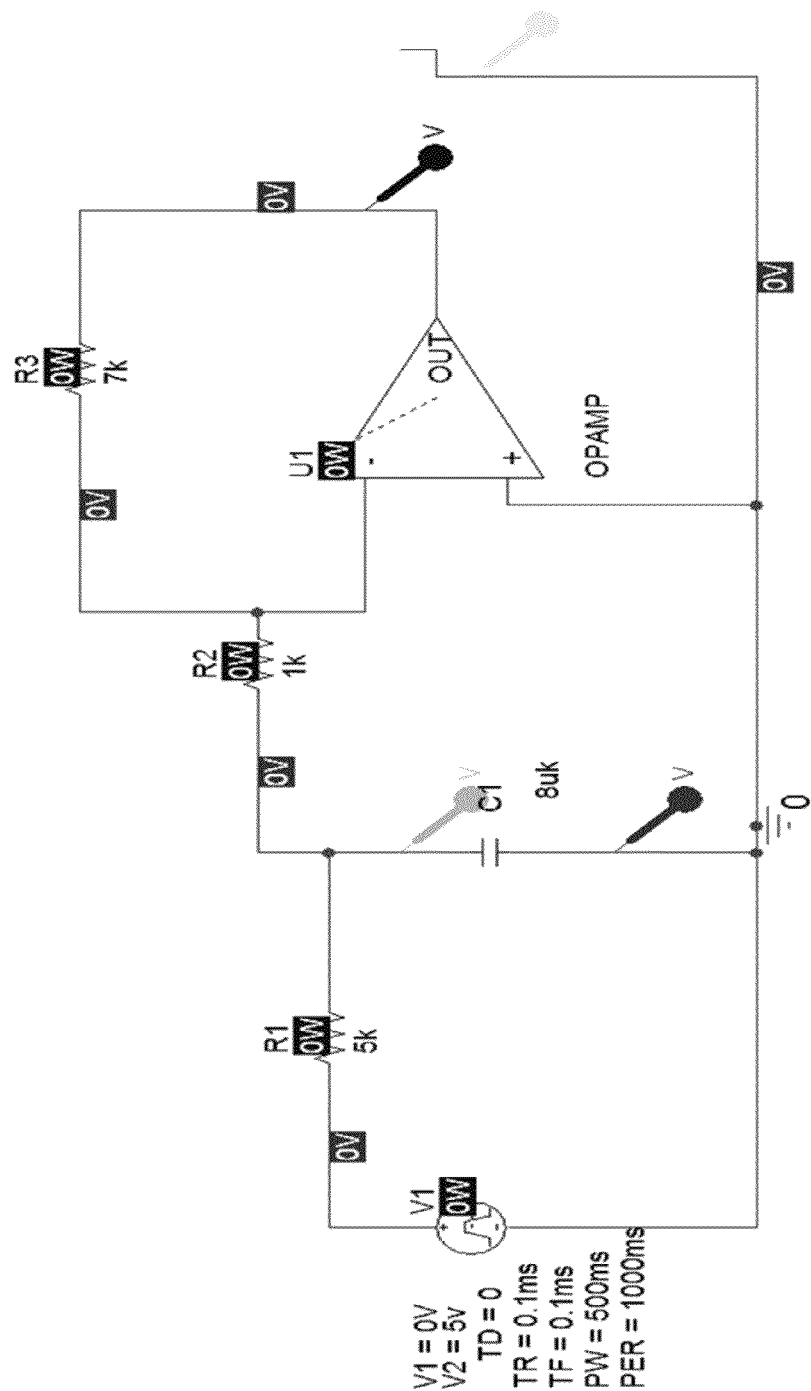
FIG. 6A shows 8 uF capacitor measurement circuit.
Figure 6B:
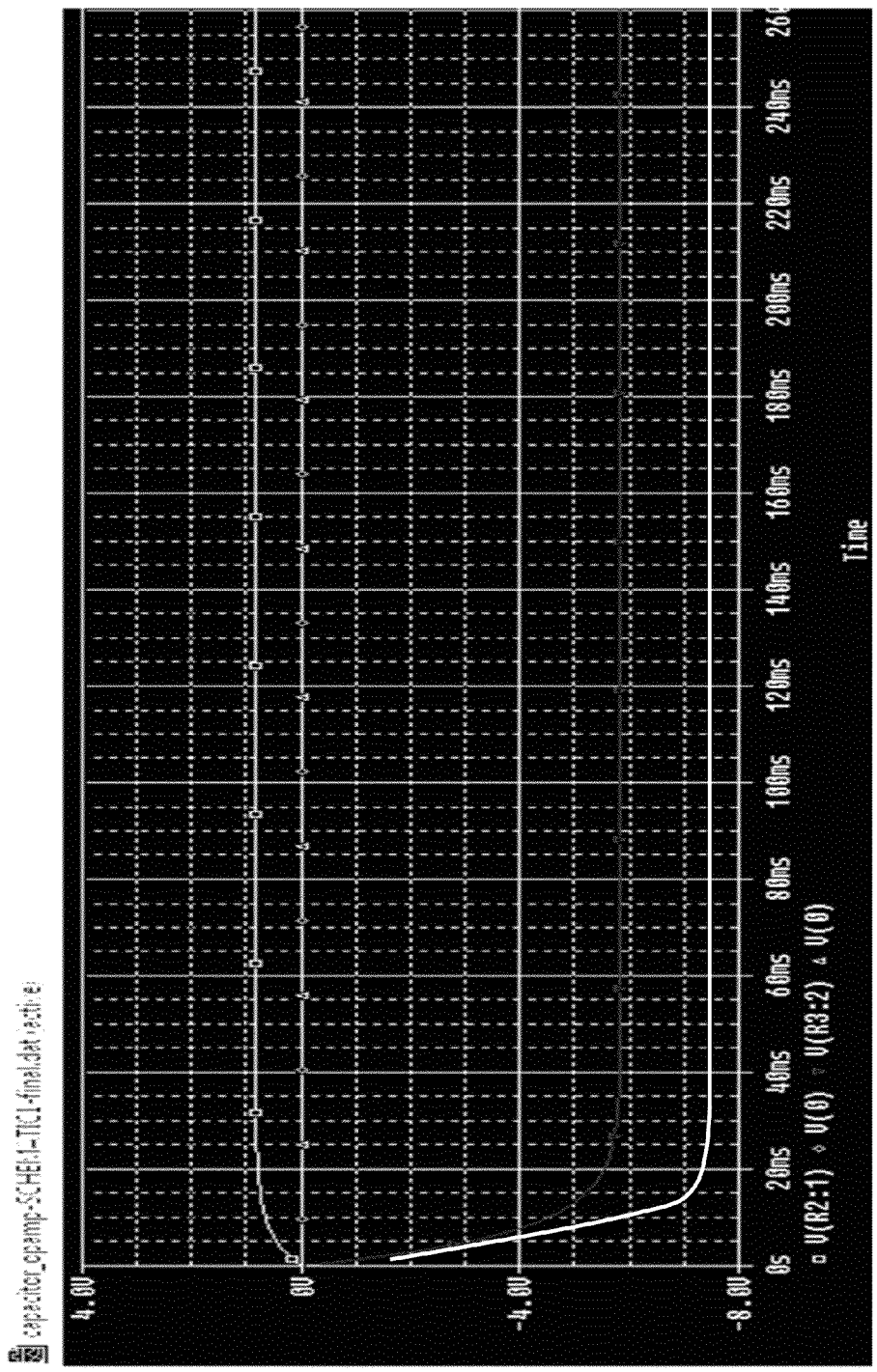
FIG. 6B is a graphical representation of FIG. 6A with inverting op amp.
Figure 7A:
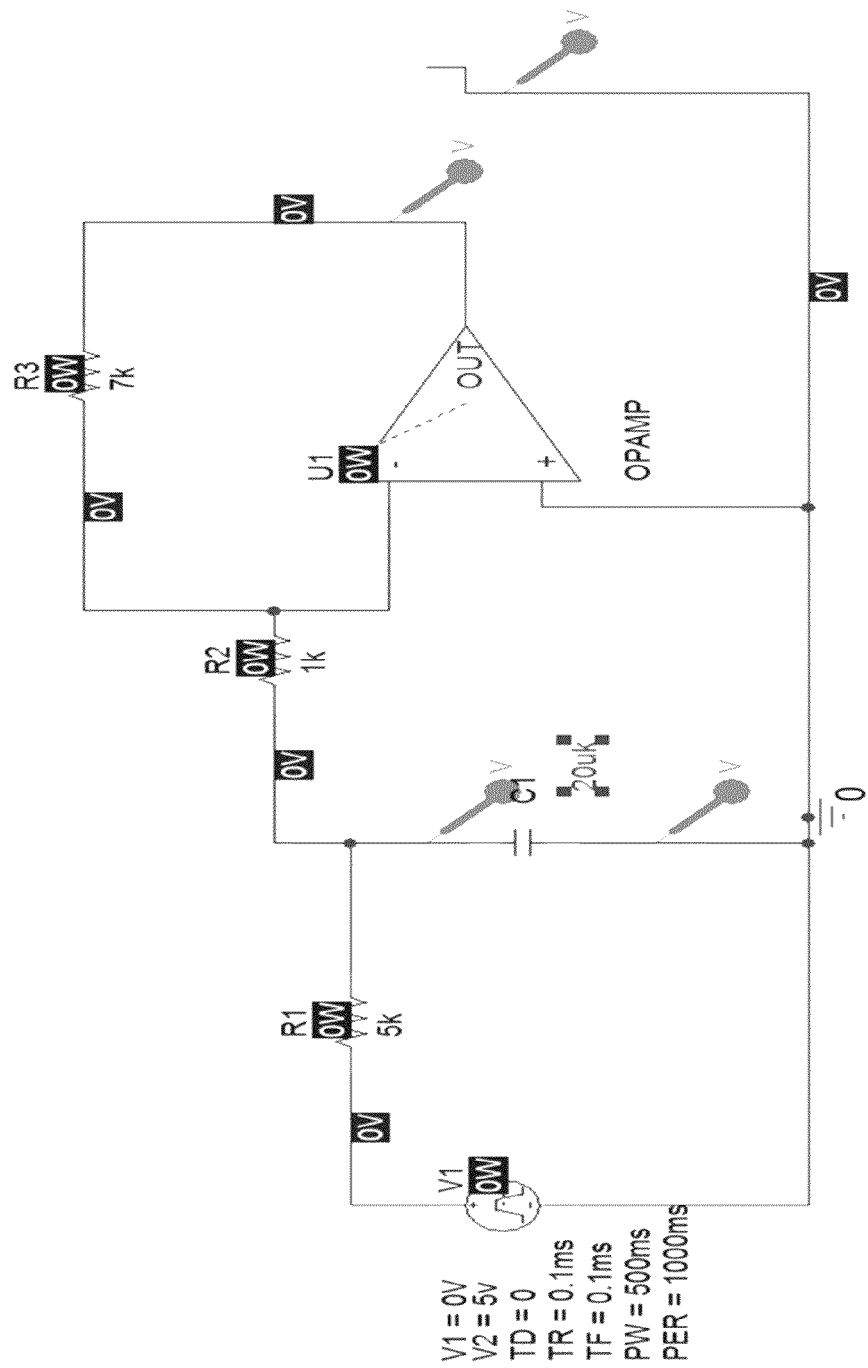
FIG. 7A shows a 20 uF capacitor measurement circuit.
Figure 7B:
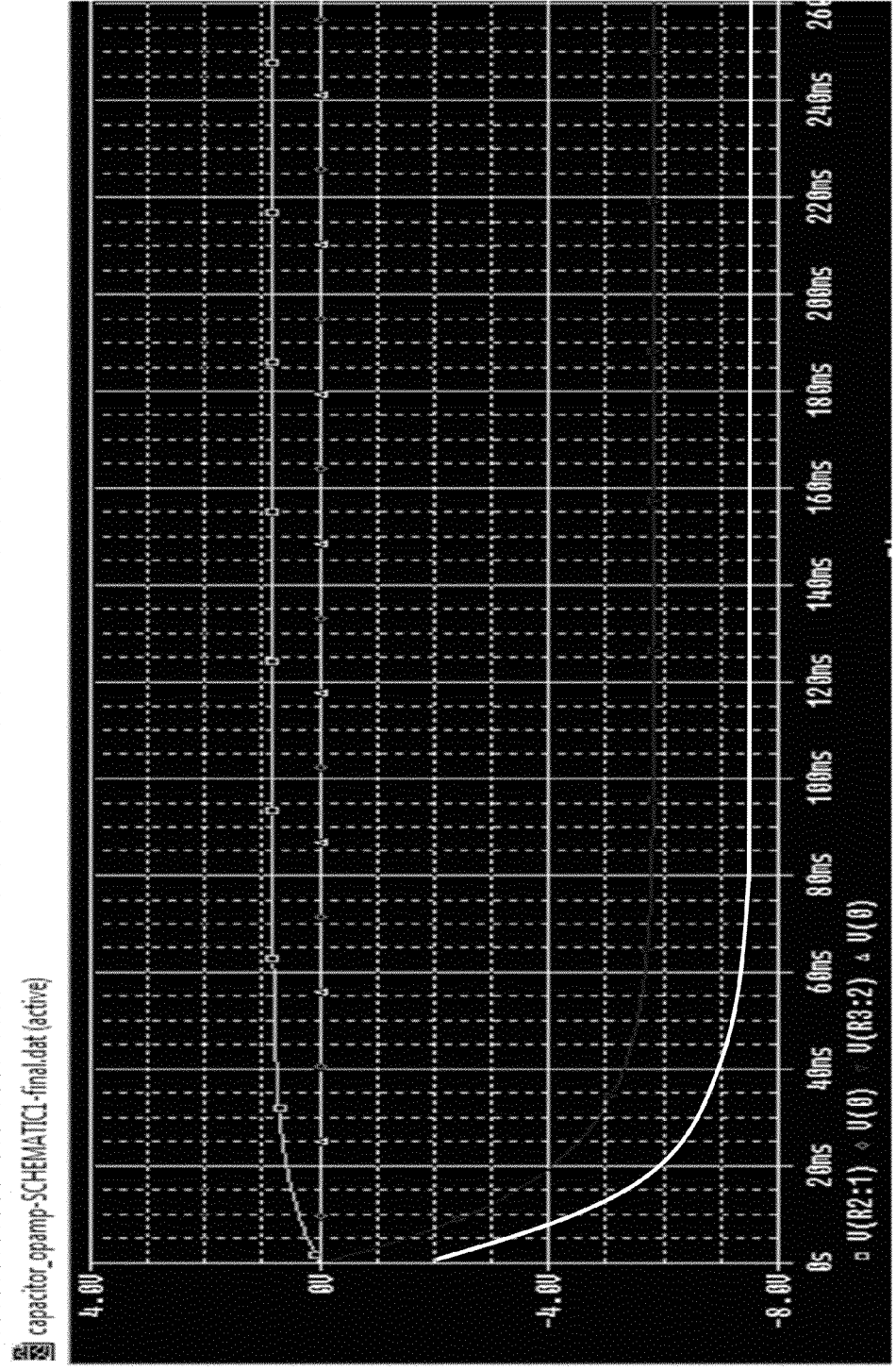
FIG. 7B is a graphical representation of FIG. 7A with inverting op amp.
Figure 8:
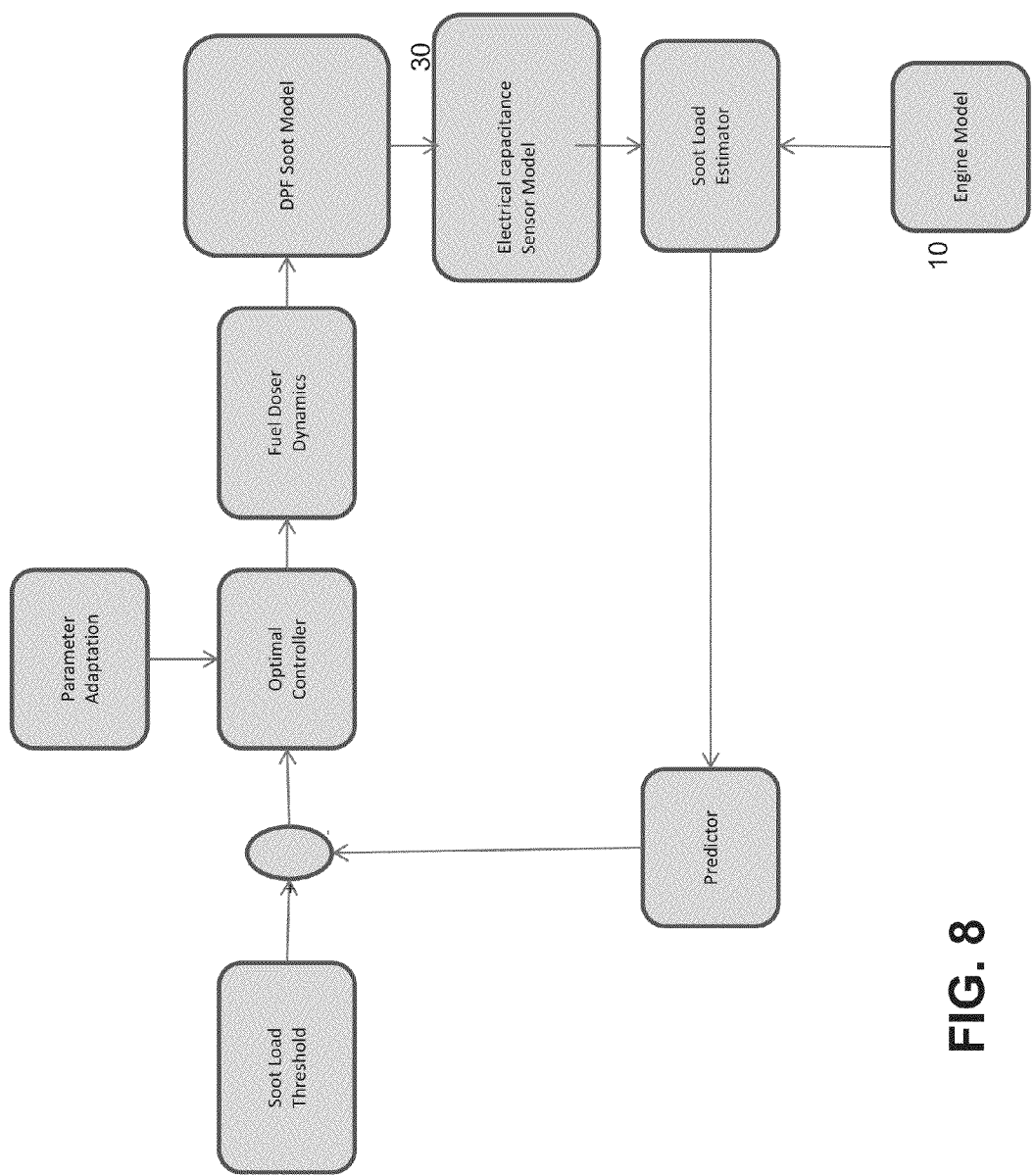
FIG. 8 is a block diagram representation of the closed loop active regeneration system for a diesel particulate filter (DPF) with electrical capacitance soot load sensor feedback.
Figure 9:
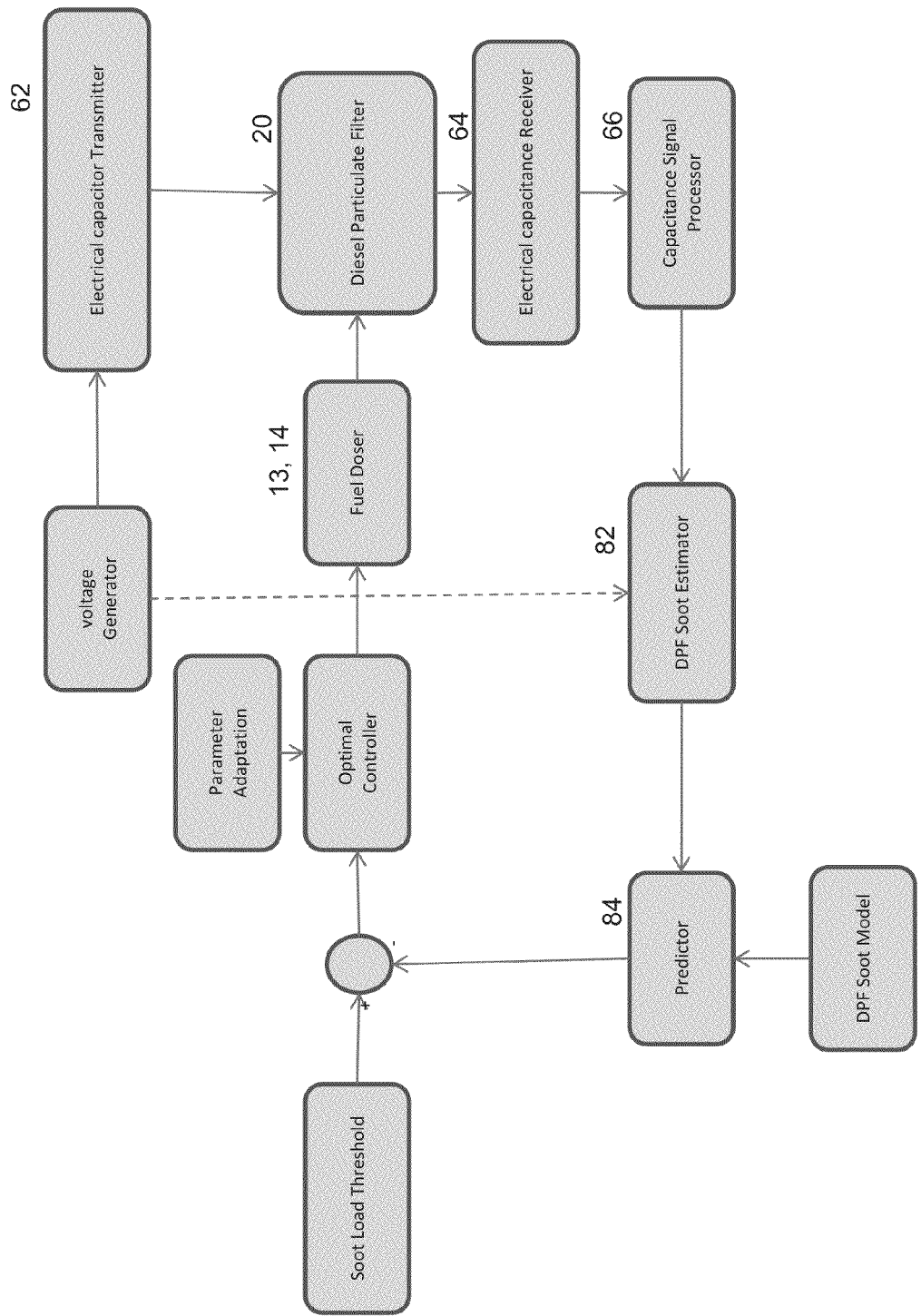
FIG. 9 is a block diagram representation of the closed loop active regeneration system for a diesel particulate filter (DPF) with electrical capacitance soot load sensor feedback.
Figure 10:
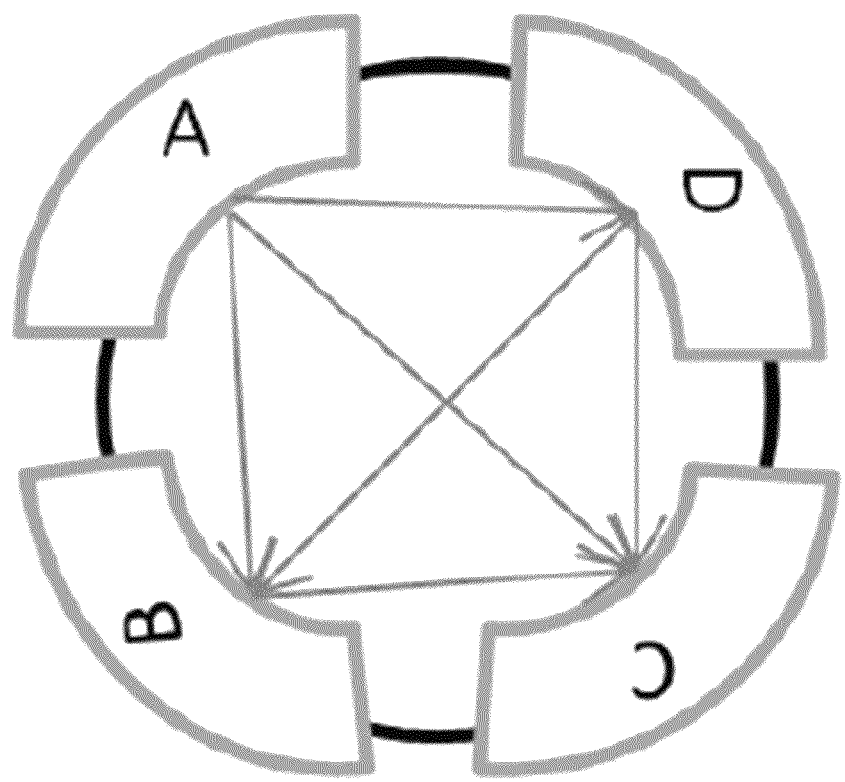
FIG. 10 shows a schematic representation of an experimental setup showing opposite voltage (A-C), and side-by-side voltage (B-D).
Figure 11A:
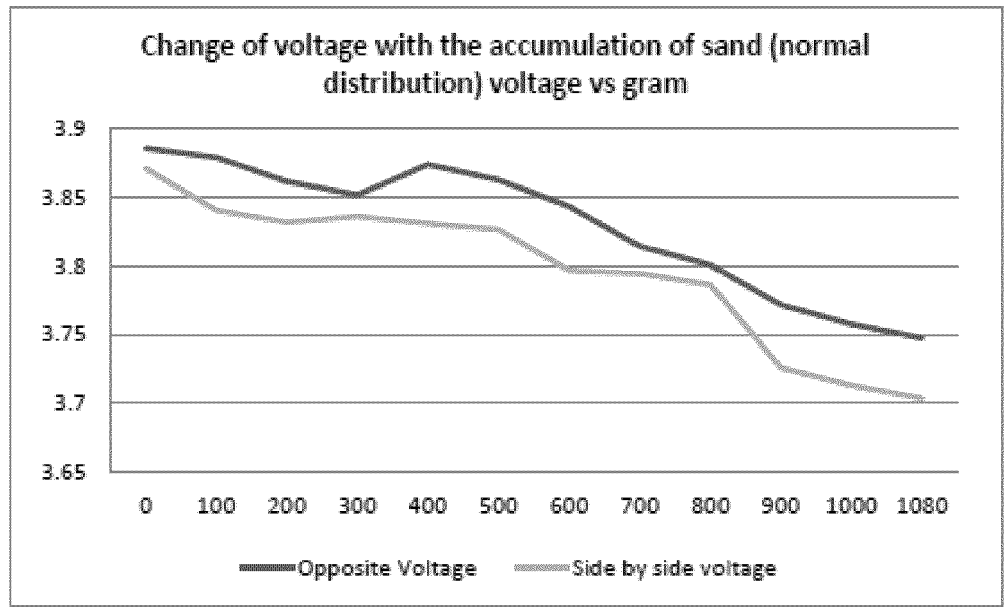
FIGS. 11A and 11B show the change in voltage for normal and concentrated distributions, respectively, of sand.
Figure 11B:
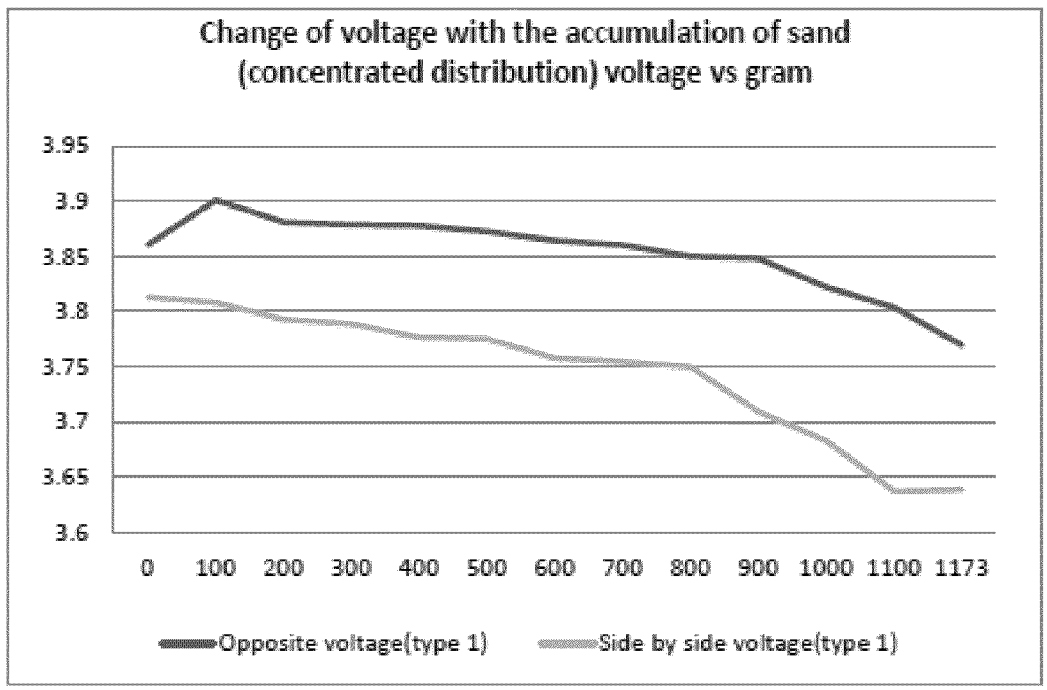
Figure 12:
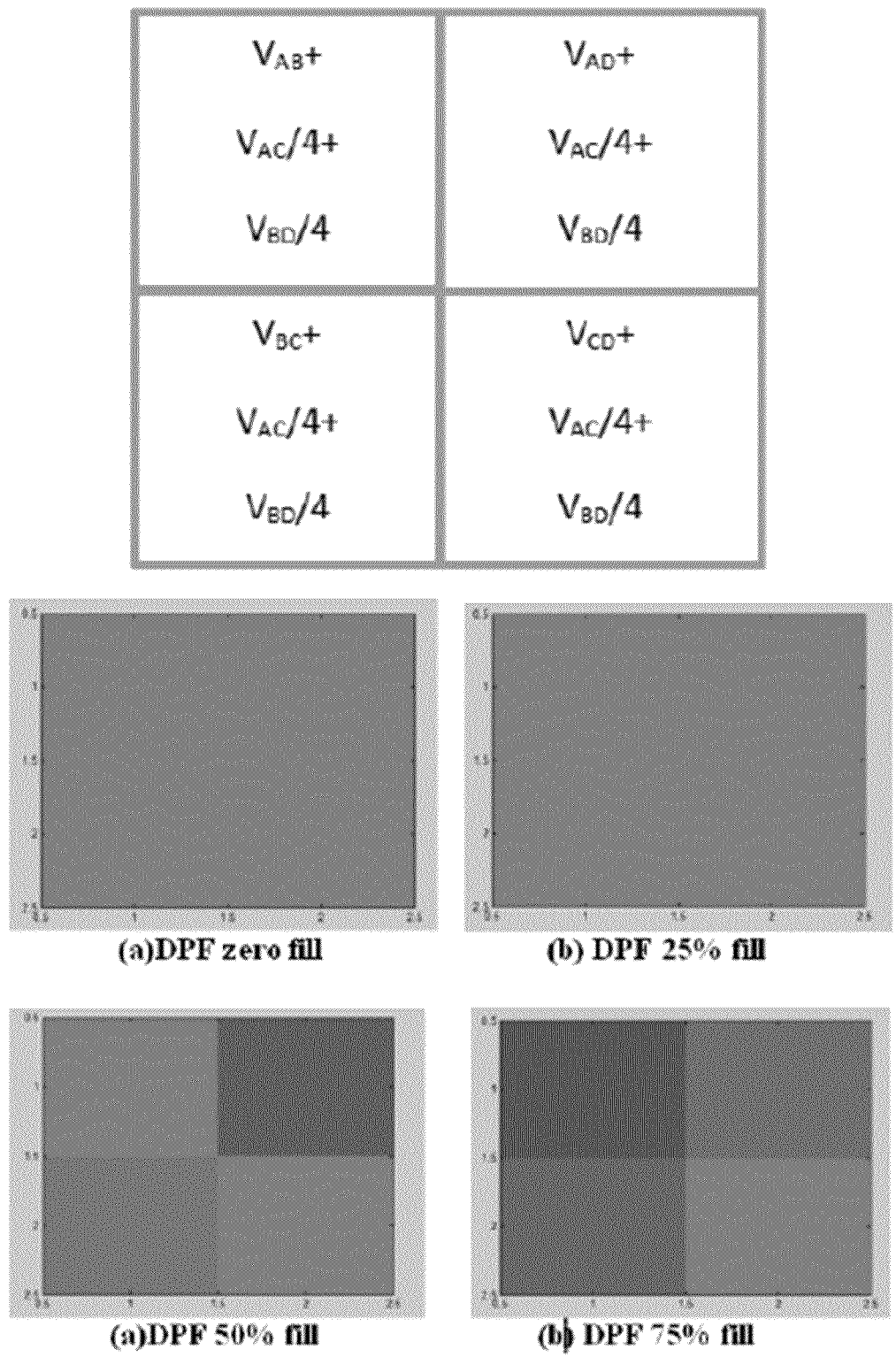
FIG. 12 shows a tomographic image generated from the data of FIG. 11 without using linear back-projection.
Figure 13:
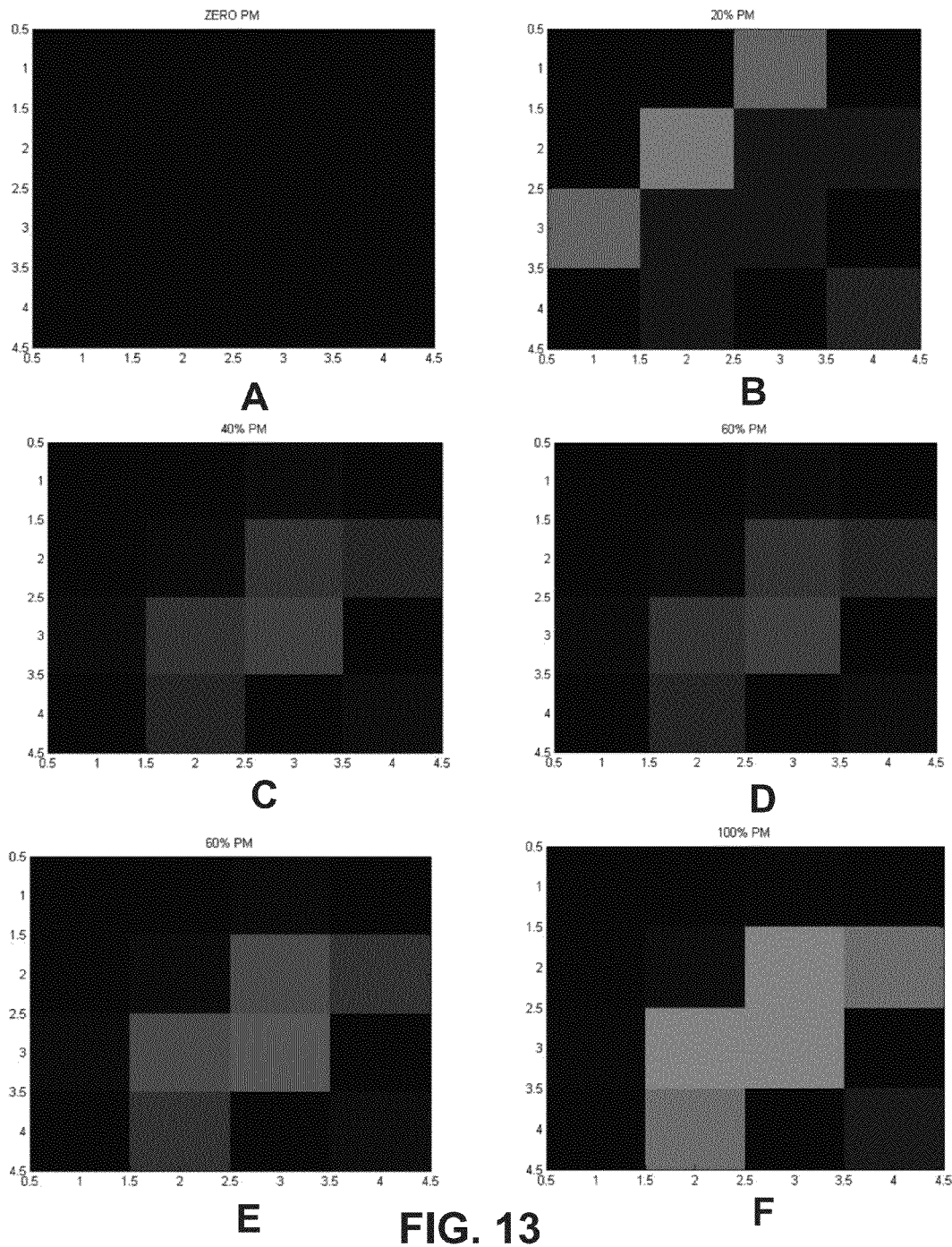

Experimental verification of one embodiment was performed with a test bench equipped with an automatic National instruments data acquisition system NI DAQ-6008 for capturing the capacitance values. Dry sand was used as a replacement of soot to verify the approach of using electrical capacitance tomography to soot detection. Two different methods of sand distribution were considered while conducting the experiments. In concentrated distribution the assumption is at first sand start accumulation near to one particular electrode, and later filled up the whole filter just. On the other hand in normal distribution the assumption is the sand distributed equally through the whole filter. Data acquisition hardware senses the change of sand accumulation by the changes of the capacitance plate voltages. Voltage signals were processed in LABVIEW and FIG. 11 is depicting the fact that with the increase of sand accumulation the voltage is also changing. FIG. 12 shows the tomographic image generation algorithm from capacitor voltage without using linear back projection and FIG. 13 shows example of tomographic image using linear back projection method.

TABLE 1

Relationship between electrodes and number of independent measurement

| No. of Electrodes | Independent measurement | Typical speed (frame S$^{-1}$) | Reference |
|---|---|---|---|
| 6 | 15 | 400 | Waterfall et al. 1996 |
| 8 | 28 | 200 | Yang et al 2004 |
| 12 | 66 | 100 | Yang et al. 1995 |
| 16 | 120 | 50 | Dyakowaski et al. 1999 |

One approach for the length of the ECT sensor is for the diameter to be smaller than the length to lessen fringe effects. The filter model used had typical dimensions of 130 mm (5 in.) diameter and 152 mm (6 in.) length.

In the microwave range, the dielectric constant of soot has a dependency on the soot layer thickness (FIG. 2-9). In this model series permittivity model has been chosen to calculate the effective permittivity of soot and air mixture.

$$\varepsilon_s = \frac{\varepsilon_r \varepsilon_o x(1-x)}{1 - x(\varepsilon_r - 1)}$$

$$C_s = \frac{A\varepsilon_s}{d}$$

In the model the length of DPF set at 6 inch, so the length of the capacitor plate will be 6 inch and for 4 capacitor plate ECT sensor the width of the capacitor plate will be 4.71 inch (approx.) and maximum distance between two plates will be 5.6 inch.

$$\varepsilon_s = \frac{58 * 854 * 10^{(-12)} * 2(1-2)}{1 - 2(5-1)}$$

$$\varepsilon_s = 1.2649 * 10^{-11}$$

$$C_s = \frac{6 * 4.71 * 1.2649 * 10^{-11}}{5.6}$$

$$C_s = 63.8301 \text{ pF}$$

A model of the soot detection system has been designed in PSpice to check the detection voltage. An AC 5 volt 1 MHz has been supplied to 3 different examples of capacitance values 60 pF (FIGS. 2-11 and 2-12), 90 pF (FIGS. 2-13 and 2-14), and 130 pF (FIGS. 2-15 and 2-16). Results are shown in Table 2 and FIG. 2-10.

TABLE 2

Output voltage for different capacitance values

| Input voltage | Capacitance | Output voltage |
|---|---|---|
| 5 Vac | 60 pF | 1.6-1.7 v |
| 5 Vac | 70 pF | 1.2-1.3 v |
| 5 Vac | 90 pF | 0.9-1.0 v |
| 5 Vac | 110 pF | 0.7-0.8 V |
| 5 Vac | 130 pF | 0.5-0.6 v |
| 5 Vac | 150 pF | 0.3-0.4 v |

Above simulation results showed that even a very small amount of soot deposition causes variation on the output voltage. Applying these capacitance values and voltage values in a linear back projection algorithm will help to build the tomographic information of a DPF.

After data acquisition device collects all the capacitance values from capacitor voltage, these values can be normalized. Assume a 4 capacitor plate used in an ECT system (FIG. 2-17(*a*)). A tomography image was constructed in a 2*2 pixel as shown in FIG. 2-17(*b*).

In one example, the sensitivity matrices are S1=[0.6; 0.2; 0.6; 0; 0.2; 0.6], S2=[0.6; 0.05; 0; 0.6; 0.2; 0], S3=[0; 0.2; 0; 0.6; 0.05; 0.6] and S4=[0; 0.05; 0.6; 0; 0.2; 0.6], as shown in FIG. 2-18. Now in a real time scenario if particulate materials accumulates inside of a DPF in the manner as shown in FIG. 2-9, then the normalized values of ECT system outputs will be C=[0.6; 0.2; 1; 0; 0.2; 0.6] with a tomographic image like FIG. 2-20.

In order to design an optimal, adaptive, and stable controller for the active regeneration process based on the real-time instantaneous soot load sensor feedback, it is helpful to design and tune the feedback control system. The control system algorithm can be established in some embodiments using computer modeling of the soot formation dynamics within the DPF as well as in modeling the electrical capacitance sensor within DPF. A simplified engine model will be incorporated in the overall simulation model. In still further embodiments, various elements of the soot formation, sensor, or engine models may be integrated into the control algorithm itself.

In an electrical capacitance sensor, the ultrasound propagates within a DPF. The DPF material has certain electrical characteristics like permittivity, impedance and conductivity. DPF's walls are typically made of ceramic materials. The walls are porous which allow exhaust flow diffuses through. Porosity of walls changes when soot accumulates on walls. This change is soot accumulation as well alter relative permittivity of inside material.

The soot formation dynamics in DPF are represented with a dynamic model. In some embodiments this model may be prepared with a methodology such as constitutive equations for particle and cylindrical soot formation, or an empirical engine-out emissions model, combined with a physical soot oxidation model to physical model in which the pressure drop signal combined with other parameters to determine the filter load. Yet, another methodology includes soot estimation via a pressure drop model. However, a preferred embodiment includes enhancing a soot formation model with electrical capacitance based soot load measurement with dynamic parameters. Since the DPF's filtering characteristics change over time (e.g. permittivity), it becomes helpful to adapt the controller parameters based on these changes for optimal performance.

Therefore, one embodiment of the present invention includes an adaptation of the controller parameters with an optimal controller that would minimize the error between the desired and measured soot load as well as the error between desired and measured back pressure. In some embodiments, fuel dosing amount with a weight can also be part of the cost function. This will allow optimal usage of fuel for dosing purposes. One following cost function, F, is proposed for the design of the optimal controller:

$$F(m_s, p_b, m_f) = \int_{t1}^{t2} \{(m_{sd} - m_s)^2 + w_1(p_{bd} - p_b)^2 + w_2 m_f^2\} dt$$

Where $m_{Sd}$ and $m_s$ are the desired and measured soot load mass, pbd and pb are the desired and measured back pressure, mf is the fuel dosing amount between time t1 and t2, and w1 and w2 are weights. The cost function is a function of input prices and output quantity. Its value is the cost of making that output given those input prices. A common form: c(w1, w2, y) is the cost of making output quantity y using inputs that cost w1 and w2 per unit. Since it is helpful to regenerate the filter by process of burning off the soot deposits as soon as needed, a long range predictive control algorithm is used which can enhance the estimates of soot load mass in DPF many time steps ahead. The predictive control algorithm thus can compensate for system dead times by taking control action at current time based on future estimates and thus providing improved overall system performance. A brief description of the long range predictive control theory follows.

A class of predictive self-tuning controllers, known as Generalized Predictive Controller (GPC) have shown robustness against unstable plants, non-minimum-phase plants, model over parameterization, and uncertain process dead time. These controllers have also been observed to provide offset free behavior for the closed loop system since they include an integral action. These set of controllers can be used in regulator or tracking-type observer applications. In the context of long range prediction, the prediction horizon, j is a tunable design variable that can be set to several time steps ahead according to the desired prediction range. The predictive nature of the GP (Generalized Prediction) based predictor algorithm comes from the use of the Diophantine equation. Through the use of Diophantine equation, the output of the system model is predicted j-step ahead of present time. This predicted output is then used to compute the control input for future time step, but is applied at present time.

For a given transfer function of a linearized soot load DPF model, a discretized version of the dynamic model of DPF can be written as:

$$A(z^{-1})Y(z) = B(z_{-1})U(z)$$

Where $A(z^{-1})$ and $B(z^{-1})$ are polynomial of order $n_a$ and $n_b$, respectively in the backward shift operator in time, $z^{-1}$. U is the control input (fuel dosing amount) and Y is the soot load mass in the DPF. $A(z^{-1})$ and $B(z^{-1})$ have the following forms:

$$A(z^{-1}) = d_0 + d_1 z^{-1} + d_2 z^{-2} + \ldots + d_{na} z^{-na}$$

$$B(z^{-1}) = n_0 + n_1 z^{-1} + n_2 z^{-2} + \ldots + n_{nb} z^{-nb}$$

In order to make a prediction of the future output of the DPF soot load, the Diophantine identity is used to derive the j-step ahead prediction of U(t+j).

$$1 = E_j(z^{-1})A(z^{-1}) + z^{-j} F_j(z^{-1})$$

Where $E_j$ and $F_j$ are uniquely defined polynomials for a given $A(z^{-1})$ and the prediction interval j. In one example, the recursive technique is used to obtain $E_j$ and $F_j$. This makes the procedure computationally efficient. It has been shown that with increasing j only the highest order term in $E_{j+1}(z^{-1})$ changes while the rest of the coefficients remain the same in $E_j(z^{-1})$.

Therefore, we can write:

$$E_{j+1}(z^{-1}) = E_j(z^{-1}) + e_j z^{-j}$$

where, $E_j(z^{-1}) = e_0 + e_1 z^{-1} + e_2 z^{-2} + \ldots + e_{j-1} z^{-(j-1)}$ In the degree of polynomial $A(z^{-1})$ is $n_a$ then the degree of $F_j(z^{-1})$ becomes $n_a$. The coefficients of the polynomial $F_j(z^{-1})$ may then be denoted as:

$$F_j(z^{-1}) = f_{j,0} + f_{j,1} z^{-1} + f_{j,2} z^{-2} + \ldots + f_{j,na} z^{-na}$$

GP based prediction is now executed for the discretized DPF model. The Diophantine prediction equation (j-step ahead predictor) is given by, $$E_j(z^1)d_0 + d_1 z^{-1} + d_2 z^{-2} + d_3 z^{-3} + d_4 z^{-4})\Delta + z^{-1} F_j(z^1) = 1$$

Multiplying the above equation with (t+j) and rearranging that equation, we obtain:

$$\theta(t+j) = F_j(z^{-1})\theta(t) - E_j(z^{-1})$$
$$(n_0 + n_1 z^{-1} + n_2 z^{-2} + n_2 z^{-3} + n_4 z^{-4})\Delta i_m(t-j+1)$$

where, $\Delta = (1 - z^{-1})$

The above equation predicts the value of the soot load mass $\theta$ in the future (j-time step ahead).

$$\theta(t+j) = F \times \theta(t) + EB \times \Delta i_m(t-j+1)$$

The matrices $F \in \mathfrak{R}^{N \times 5}$ and $EB \in \mathfrak{R}^{N \times (N+5)}$ can be calculated by, for example, using a MATLAB script.

With aging of the DPF, the filter characteristics may change in order to provide sustained optimal performance of the proposed control system. Various updates include an update of the controller parameters (within allowable limits) based on periodic on-line identification of the DPF system model parameters. A Recursive Least Squares (RLS) methodology can be utilized for this functionality. FIGS. 8 and 9 show various representations of the closed loop regeneration systems based on analytical models. The controller parameters can be tuned via simulation experiments. In addition, a dSPACE real-time controller can be used to implement the model in FIGS. 8 and 9 in real-time.

Figure 1B:
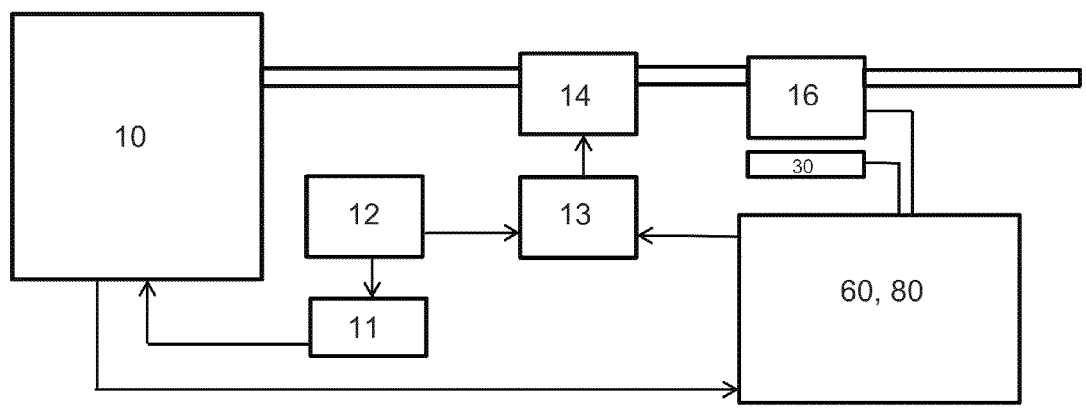
FIG. 1B is a block diagram of a system according to one embodiment of the present invention.

FIG. 1B presents a simplified block diagram of a system according to one embodiment of the present invention. An engine 10 such as a diesel engine is provided with fuel from a source 12 by means of an electrically actuated fuel system 11 under the control of an engine controller 60 which preferably operates with a plurality of control algorithms 80. Controller 60 further receives a variety of feedback signals from engine 10 used in the control of the fuel system 11.

Exhaust from engine 10 is provided in some embodiments to a heating member 14 such as a catalytic chamber that is provided with fuel from source 12 by way of a fuel component 13 operably controlled by algorithms 80 of controller 60. When fuel is applied by injector 13 to catalyst 14, there is a subsequent heating of the exhaust and therefore of the diesel particulate filter 16. Exhaust gases from engine 10 are ultimately passed to ambient conditions by way of DPM 16. It is further understood that various algorithms and sensors described herein are further applicable to those embodiments in which the method of heating the catalytic chamber 14 is by way of modified engine fuel schedule, microwave heating, or any other means of heating the filter 16.

FIGS. 1B, 2, and 3 depict various views of a capacitive sensor system 20 according to one embodiment of the present invention. Particulate sensing system 20 includes a diesel particulate filter 16 preferably having a plurality of capacitive sensors 30, although it is understood that in some embodiments sensing system 20 can include a single capacitive element.

Sensing system 20 shows a plurality of cylindrically plates 32 and 34 surrounding a central filter element 16, all of which is enclosed within the protective housing 21. In one embodiment, a driver 62 of controller 60 provides an alternating voltage source to at least one of the plates 32. The application of this voltage field to plate 32 establishes an electrical field extending to each of the plurality of the other cylindrically shaped and circumferentially disposed second electrodes 34. This electrical field is modified by the presence of particulate matter within filter 16. Each of the second electrodes 34 is in electrical communication with a capacitance receiver 64 within controller 60. A capacitance signal processor 66 within controller 60 (as best seen on FIG. 9) provides a signal corresponding to the measured capacitance between the corresponding plates 32 and 34. This signal is a term provided to a soot estimator 82 within algorithm 80. An estimation of the soot state of filter 16 is then provided to a predictor 84, after which control algorithm 80 determines whether or not to actuate fuel doser 13 to heat catalytic chamber 14. It is further understood that although a sensor 30 has been shown and described with one of the capacitive electrodes being in communication with a voltage source and a plurality of other capacitive plates being in electrical communication with a measurement device, it is further appreciated that yet other configurations are envisioned, including multiple pairings of plates 32 and 34.

Various aspects of different embodiments of the present invention are expressed in paragraphs X1, X2, X3, X4 and X5 as follows:

X1. Once aspect of the present invention pertains to a method for sensing, comprising providing a filter having a flowpath therethrough and a media for trapping material in the flowpath, the media having a plurality of sides, a first electrically conductive plate on a side of the flowpath, a second electrically conductive plate on a side of the flowpath, a third electrically conductive plate a side of the flowpath, each of the first, second, and third plates being spaced apart from one another, and a voltage source having a signal lead and a common lead and capable of supplying a transient voltage to the signal lead relative to the common lead; placing the first plate in electrical communication with the signal lead; placing the second plate and the third plate in electrical communication with the common lead, applying an input transient voltage with the source to the signal lead; measuring the capacitance of the second plate relative to the first plate; and measuring the capacitance of the third plate relative to the first plate.

X2. Another aspect of the present invention pertains to an apparatus for sensing, comprising a filter for filtering particulate matter from a gaseous stream, said filter having filtering media and a flowpath for the gaseous stream through the media; a first electrically conductive plate in electrical communication with a first lead; and a second electrically conductive plate in electrical communication with a second lead, said first plate and the first lead being electrically isolated from said second plate and the second lead, said first plate and said second plate being spaced apart from each other with a first portion of the media and the flowpath being between said first plate and said second plate.

X3. Another aspect of the present invention pertains to a method for sensing, comprising providing a filter having a flowpath therethrough and a media for trapping material in the flowpath; a first capacitor having a pair of spaced apart plates and a first portion of the media and flowpath therebetween; a second capacitor having a pair of spaced apart plates and a second portion of the media and flowpath therebetween, the second portion being different than the first portion; measuring a first capacitance with the first capacitor, the first capacitance corresponding at least in part to the amount of material trapped in the first portion of the media; and measuring a second capacitance with the second capacitor, the second capacitance corresponding at least in part to the amount of material trapped in a second portion of the media.

X4. Yet another aspect of the present invention pertains to a method for sensing, comprising providing a filter having a flowpath therethrough and a porous media for trapping material in the flowpath; placing a spatially distributed plurality of capacitive plates around the flowpath, such that different portions of the porous media and trapped material act as dielectric material between different pairs of the plates; sequentially applying an alternating voltage across different pairs of plates; measuring the capacitance of each of the pairs of plate during said applying; and preparing a dataset corresponding to the distributed capacitance of the filter.

X5. Still another aspect of the present invention pertains to a method for sensing, comprising providing an object having a volume with a distributed mass therein; placing a spatially distributed plurality of capacitive plates around the object, such that different portions of the distributed mass act as dielectric material between different pairs of the plates; sequentially applying an alternating voltage across different pairs of plates; measuring the capacitance of each of the pairs of plate during said applying; and preparing a dataset corresponding to the distributed mass of the object.

Yet other embodiments pertain to any of the previous statements X1, X2, X3, X4, and X5 which are combined with one or more of the following other aspects. It is also understood that any of the aforementioned X paragraphs include listings of individual features that can be combined with individual features of other X paragraphs.

Wherein said measuring the second capacitance and said measuring the second capacitance are simultaneous.

Wherein said measuring the second capacitance and said measuring the second capacitance are sequential.

Wherein the media has a periphery, and the first, second, and third plates are spaced apart from one another along the periphery.

Which further comprises measuring the capacitance of the second plate relative to the third plate.

Which further comprises a third electrically conductive plate in electrical communication with a third lead, said third plate and the third lead being electrically isolated from said first plate and said second lead, said first plate and said third plate being spaced apart from each other with a second portion of the media and the flowpath being between said first plate and said third plate, the first portion being different than the second portion.

Wherein said second lead and said third lead share a common electrical connection, and which further comprises a source of alternating voltage, said source providing an alternating voltage to said first lead relative to the common connection.

Wherein said filter media has a pair of opposing sides, said first plate is on a first side, and said second plate and said third plate are on a second side generally opposite of the first side.

Wherein said filtering media has a generally circular cross section, and said first, second, and third plates are circumferentially spaced apart from each other.

Which further comprises a source of alternating voltage, said source providing an alternating voltage to said first lead relative to said second lead.

Wherein the gaseous stream is the exhaust of a diesel engine.

Wherein said first capacitor and said second capacitor share a common plate.

Which further comprises determining the amount of material trapped in the media by said first measuring and said second measuring.

Which further comprises establishing a time history of a plurality of said first measuring and a plurality of said second measuring, and said determining is with the time history.

Wherein the flowpath is a gaseous flowpath.

Wherein the flowpath is for exhaust from an engine and the material is particulate material.

Wherein the dataset is a first dataset, and which further comprises flowing a gas including particulate matter through the flowpath, preparing a second dataset, and comparing the first dataset and second dataset and determining the changes in capacitance.

Which further comprises preparing a tomographic representation of the filter from the dataset.

Wherein the object is fabricated from an inorganic material having a predetermined mass distribution.

Wherein the object is a filter in an industrial facility.

Wherein the object is part of a prosthetic joint.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method for sensing, comprising:
providing a filter having a flowpath therethrough and a media for trapping material in the flowpath, the media having a plurality of sides, a first electrically conductive plate on a side of the flowpath, a second electrically conductive plate on a side of the flowpath, a third electrically conductive plate on a side of the flowpath, each of the first, second, and third plates being spaced apart from one another, and a voltage source having a signal lead and a common lead and capable of supplying a transient voltage to the signal lead relative to the common lead;
placing the first plate in electrical communication with the signal lead;
placing the second plate and the third plate in electrical communication with the common lead;
applying an input transient voltage with the source to the signal lead;
measuring the capacitance of the second plate relative to the first plate; and
measuring the capacitance of the third plate relative to the first plate.

2. The method of claim 1 wherein said measuring the second capacitance and said measuring the second capacitance are simultaneous.

3. The method of claim 1 wherein said measuring the second capacitance and said measuring the second capacitance are sequential.

4. The method of claim 1 wherein the media has a periphery, and the first, second, and third plates are spaced apart from one another along the periphery.

5. The method of claim 1 which further comprises measuring the capacitance of the second plate relative to the third plate.

6. The method of claim 1 wherein the first, second, and third plates are disposed outside of the filter.

7. An apparatus for sensing, comprising:
a filter for filtering particulate matter from a gaseous stream, said filter having filtering media and a flowpath for the gaseous stream through the media;
a first electrically conductive plate in electrical communication with a first lead;
a second electrically conductive plate in electrical communication with a second lead, said first plate and the first lead being electrically isolated from said second plate and the second lead, said first plate and said second plate being spaced apart from each other with a first portion of the media and the flowpath being between said first plate and said second plate;
a third electrically conductive plate in electrical communication with a third lead, said third plate and the third lead being electrically isolated from said first plate and said second lead, said first plate and said third plate being spaced apart from each other with a second portion of the media and the flowpath being between said first plate and said third plate, the first portion being different than the second portion, wherein said second lead and said third lead share a common electrical connection; and
a source of alternating voltage, said source providing an alternating voltage to said first lead relative to the common connection.

8. The apparatus of claim 7 wherein said filter media has a pair of opposing sides, said first plate is on a first side, and said second plate and said third plate are on a second side generally opposite of the first side.

9. The apparatus of claim 7 which further comprises a second source of alternating voltage, said second source providing an alternating voltage to said first lead relative to said second lead.

10. The apparatus of claim 7 wherein the gaseous stream is the exhaust of a diesel engine.

11. The apparatus of claim 7 wherein the first, second, and third plates are disposed outside of the filter.

12. The apparatus of claim 7 wherein the first, second, and third plates are disposed at substantially same points along the flowpath.

13. An apparatus for sensing, comprising:
a filter for filtering particulate matter from a gaseous stream, said filter having filtering media and a flowpath for the gaseous stream through the media, wherein said filtering media has a generally circular cross section;
a first electrically conductive plate in electrical communication with a first lead;
a second electrically conductive plate in electrical communication with a second lead, said first plate and the first lead being electrically isolated from said second plate and the second lead, said first plate and said second plate being spaced apart from each other with a first portion of the media and the flowpath being between said first plate and said second plate; and
a third electrically conductive plate in electrical communication with a third lead, said third plate and the third lead being electrically isolated from said first plate and said second lead, said first plate and said third plate being spaced apart from each other with a second portion of the media and the flowpath being between said first plate and said third plate, the first portion being different than the second portion, wherein said first, second, and third plates are circumferentially spaced apart from each other.

14. A method for sensing, comprising:
- providing a filter having a flowpath therethrough and a media for trapping material in the flowpath;
- providing a first capacitor having a pair of spaced apart plates and a first portion of the media and flowpath therebetween;
- providing a second capacitor having a pair of spaced apart plates and a second portion of the media and flowpath therebetween, the second portion being different than the first portion;
- measuring a first capacitance with the first capacitor, the first capacitance corresponding at least in part to the amount of material trapped in the first portion of the media; and
- measuring a second capacitance with the second capacitor, the second capacitance corresponding at least in part to the amount of material trapped in a second portion of the media.

15. The method of claim 14 wherein said first capacitor and said second capacitor share a common plate.

16. The method of claim 14 which further comprises determining the amount of material trapped in the media, the determining being based on said first measuring and said second measuring.

17. The method of claim 16 which further comprises establishing a time history of a plurality of said first measuring and a plurality of said second measuring, and said determining is with the time history.

18. The method of claim 14 wherein the flowpath is a gaseous flowpath for exhaust from an engine and the material is particulate material.

19. A method for sensing, comprising:
- providing a filter having a flowpath therethrough and a porous media for trapping material in the flowpath;
- placing a spatially distributed plurality of capacitive plates around the flowpath, such that different portions of the porous media and trapped material act as dielectric material between different pairs of the plates;
- sequentially applying an alternating voltage across different pairs of plates;
- measuring the capacitance of each of the pairs of plate during said applying; and
- preparing a dataset corresponding to the distributed capacitance of the filter.

20. The method of claim 19 wherein the dataset is a first dataset, and which further comprises flowing a gas including particulate matter through the flowpath, preparing a second dataset, and comparing the first dataset and second dataset and determining the changes in capacitance.

21. The method of claim 19 which further comprises preparing a tomographic representation of the filter from the dataset.

* * * * *